(12) United States Patent  
Hiraide

(10) Patent No.: US 10,172,512 B2  
(45) Date of Patent: Jan. 8, 2019

(54) CAPSULE ENDOSCOPE HAVING ARRANGED ILLUMINATION CONTROL CIRCUITS WITH WIRING BETWEEN THE CIRCUITS

(71) Applicant: OLYMPUS CORPORATION, Hachioji-shi, Tokyo (JP)

(72) Inventor: Shuzo Hiraide, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 134 days.

(21) Appl. No.: 15/236,959

(22) Filed: Aug. 15, 2016

(65) Prior Publication Data

US 2016/0345810 A1   Dec. 1, 2016

Related U.S. Application Data

(63) Continuation of application No. PCT/JP2015/057335, filed on Mar. 12, 2015.

(30) Foreign Application Priority Data

Mar. 28, 2014 (JP) .................... 2014-068378

(51) Int. Cl.
  *A61B 1/06* (2006.01)
  *A61B 1/04* (2006.01)
  (Continued)

(52) U.S. Cl.
  CPC ............ *A61B 1/041* (2013.01); *A61B 1/005* (2013.01); *A61B 1/0011* (2013.01); *A61B 1/051* (2013.01);
  (Continued)

(58) Field of Classification Search
  CPC ......... A61B 1/041; A61B 1/05; A61B 1/0676; A61B 1/051; A61B 1/00006;
  (Continued)

(56) References Cited

U.S. PATENT DOCUMENTS

| 2003/0011625 A1* | 1/2003 | Kellis .................. G09G 3/32 |
| | | 345/690 |
| 2003/0030180 A1* | 2/2003 | Meek .................. H04N 5/2252 |
| | | 264/272.14 |

(Continued)

FOREIGN PATENT DOCUMENTS

| EP | 1 627 592 A1 | 2/2006 |
| EP | 2 752 147 A1 | 7/2014 |

(Continued)

OTHER PUBLICATIONS

International Search Report dated Jun. 9, 2015, counterpart International Application No. PCT/JP2015/057335, with English translation (4 pages).

*Primary Examiner* — John P Leubecker
(74) *Attorney, Agent, or Firm* — Westerman, Hattori, Daniels & Adrian, LLP

(57) ABSTRACT

A capsule endoscope includes a flexible substrate which is integrally formed by disposing an illumination substrate section, a first wiring substrate section, an imaging element substrate, a second wiring substrate section, and a signal-processing substrate section in a row in sequence and an illumination control circuit which includes an illumination control signal output unit and an illumination driving unit, wherein the light-emitting elements are LEDs, wherein the illumination driving unit is disposed on the imaging element substrate section or the illumination substrate section, and wherein the illumination driving unit includes a transistor array which is formed by a plurality of transistors, the plurality of transistors corresponding to each of the light-emitting elements provided in the illumination unit and generating illumination currents in accordance with the illumination control signal.

6 Claims, 13 Drawing Sheets

(51) Int. Cl.
*A61B 1/05* (2006.01)
*A61B 1/005* (2006.01)
*H04N 5/225* (2006.01)
*A61B 1/00* (2006.01)

(52) U.S. Cl.
CPC ....... *A61B 1/00006* (2013.01); *A61B 1/00009* (2013.01); *A61B 1/0684* (2013.01); *H04N 5/2256* (2013.01)

(58) Field of Classification Search
CPC ............ A61B 1/0684; A61B 2090/309; G02B 23/2461; H04N 5/2256
See application file for complete search history.

(56) References Cited

U.S. PATENT DOCUMENTS

| | | | | |
|---|---|---|---|---|
| 2005/0049488 | A1 | 3/2005 | Homan | |
| 2006/0020168 | A1* | 1/2006 | Naruse | A61B 1/00027 600/179 |
| 2006/0104057 | A1* | 5/2006 | Avron | A61B 1/0011 362/227 |
| 2007/0008255 | A1* | 1/2007 | Emek | H05B 33/0815 345/82 |
| 2007/0039077 | A1* | 2/2007 | Takami | A61B 1/0638 600/180 |
| 2007/0100202 | A1* | 5/2007 | Murata | A61B 1/00059 600/109 |
| 2007/0225560 | A1* | 9/2007 | Avni | A61B 1/00006 600/118 |
| 2007/0244366 | A1* | 10/2007 | Murata | A61B 1/00105 600/175 |
| 2008/0170846 | A1* | 7/2008 | Wang | A61B 1/00096 396/182 |
| 2008/0297059 | A1* | 12/2008 | Nisani | A61B 1/00036 315/185 R |
| 2009/0303319 | A1* | 12/2009 | Sato | A61B 1/00158 348/65 |
| 2013/0141013 | A1* | 6/2013 | Kodama | H05B 33/0857 315/294 |
| 2013/0225922 | A1* | 8/2013 | Schentag | A61B 1/00186 600/109 |
| 2013/0249422 | A1* | 9/2013 | Kerstens | H05B 33/0815 315/193 |

FOREIGN PATENT DOCUMENTS

| | | |
|---|---|---|
| JP | 2002-319707 A | 10/2002 |
| JP | 2004-350963 A | 12/2004 |
| JP | 2005-73934 A | 3/2005 |
| JP | 2005-204802 A | 8/2005 |
| JP | 2007/126429 A2 | 11/2007 |
| JP | 2009-531072 A | 9/2009 |
| WO | 2013/031300 A1 | 3/2013 |

* cited by examiner

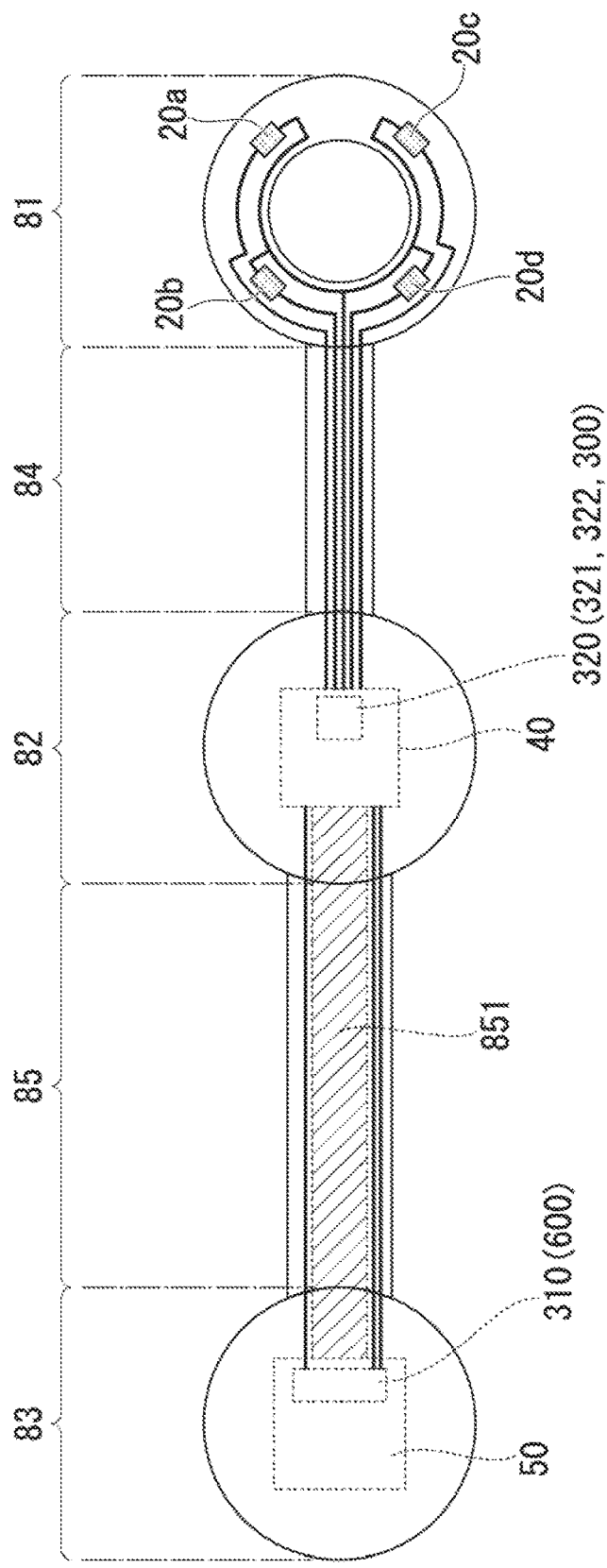

CAPSULE ENDOSCOPE HAVING ARRANGED ILLUMINATION CONTROL CIRCUITS WITH WIRING BETWEEN THE CIRCUITS

This application is a continuation application based on a PCT International Application No. PCT/JP2015/057335, filed on Mar. 12, 2015, whose priority is claimed on Japanese Patent Application No. 2014-068378, filed on Mar. 28, 2014. The contents of both the PCT International Application and the Japanese Patent Application are incorporated herein by reference.

BACKGROUND OF THE INVENTION

Field of the Invention

The present invention relates to a capsule endoscope, and more particularly, to disposition of illumination control circuits installed in a capsule endoscope and a wiring between the circuits.

Description of Related Art

In the related art, to examine the inside of a body, a capsule endoscope has been used in which an endoscope system provided by an illumination unit, an optical system, an imaging element, a signal-processing unit, a communication antenna, a power supply, and so on, is provided in a tubular capsule housing having hemispherical end portions.

In such a capsule endoscope, components that configure the endoscope system are mounted at positions separated in a flexible substrate formed as one substrate. In such a capsule endoscope, a wiring region in the flexible substrate is formed such that wirings configured to perform transmission and reception of signals between the components are formed in the wiring region, and the wiring region in the flexible substrate is accommodated in the capsule housing in a state of being folded to form a mountain fold or a valley fold. The flexible substrate usually has three component mounting region provided by an illumination substrate section on which the illumination unit is mounted, an imaging element substrate section on which the imaging element is mounted and a signal-processing substrate section on which the signal-processing unit is mounted, and two wiring regions disposed between the component mounting regions. More specifically, the flexible substrate is integrally formed in a shape in which the substrate sections are arranged in a row in sequence of the illumination substrate section, the wiring region (hereinafter, referred to as "a first wiring substrate section") between the illumination substrate section and the imaging element substrate section, the imaging element substrate section, the wiring region (hereinafter, referred to as "a second wiring substrate section") between the imaging element substrate section and the signal-processing substrate section, and the signal-processing substrate section.

The illumination unit provided in the capsule endoscope is provided by a plurality of white LEDs (light-emitting diodes) serving as the light-emitting element to radiate light to a subject to be photographed, which are connected to each other in parallel, and the white LEDs are disposed at predetermined intervals in the illumination substrate section. An LED-driving circuit provided in the signal-processing unit controls brightness of light emitted by the white LEDs by controlling a voltage of the white LEDs. When a voltage is directly applied to the white LEDs, since the white LEDs are broken by overcurrent, resistive elements configured to prevent breakage due to the overcurrent are serially connected to the white LEDs. That is, the illumination unit has a configuration in which a plurality of sets, each in which the resistive elements and the white LEDs are serially connected (hereinafter, referred to as "a white LED group"), are connected to each other in parallel.

In LEDs, there is a deviation in forward drop voltage. When the signal-processing unit applies a predetermined constant voltage to each of the white LED groups, a deviation occurs in the voltage applied to the resistive elements in the white LED groups due to the influence of the deviation of the forward drop voltages of the white LEDs. Accordingly, the current flowing through the resistive elements and the white LEDs deviates at each of the white LED groups, and a deviation also occurs even in the brightness of the light emitted from the white LED. In the capsule endoscope, it is not a suitable state since the light (the illumination light) cannot be uniformly irradiated to the photographed subject, when the brightness of the white LEDs provided in the illumination unit has variance in light emission luminance.

Therefore, a technology to control light emission of an LED using current is considered, as disclosed in Japanese Unexamined Patent Application, First Publication No. 2002-319707. In the technology disclosed in Japanese Unexamined Patent Application, First Publication No. 2002-319707, an LED-driving circuit provided by a constant current-generating circuit and a current mirror circuit corresponding to LEDs to cause the same current to flow to the LEDs is disclosed. Since the configuration of the LED-driving circuit disclosed in Japanese Unexamined Patent Application, First Publication No. 2002-319707 is applied to the signal-processing unit as the LED-driving circuit configured to control the illumination unit provided in the capsule endoscope, the plurality of white LEDs that configure the illumination unit can be driven at a low voltage in a state in which a deviation in brightness is suppressed. In such a capsule endoscope, it is possible to increase a number of the white LEDs to improve the brightness (luminance) and the uniformity of the illumination light irradiated onto the subject. In the disclosed technology, light emission of the LEDs is controlled by using the current by one ground signal commonly connected to cathode terminals of all of the LEDs and signals of current mirror circuits connected to anode terminals of the LEDs, respectively, i.e., signal lines corresponding to the number of LEDs+1. In addition, as described above, in the capsule endoscope, control of the illumination unit is performed by the LED-driving circuit provided in the signal-processing unit. Accordingly, the signals configured to control the illumination unit that configures the capsule endoscope are input into the illumination unit mounted on the illumination substrate section from the signal-processing unit mounted on the signal-processing substrate section through the second wiring substrate section, the imaging element substrate section and the first wiring substrate section.

When the technology of the LED-driving circuit disclosed in Japanese Unexamined Patent Application, First Publication No. 2002-319707 is applied to the capsule endoscope, if the number of the white LEDs is increased to achieve improvement in brightness (luminance) of the light irradiated onto the subject or uniformity of the illumination light, a larger amount of signals for the illumination unit pass through the second wiring substrate section, the imaging element substrate section and the first wiring substrate section. That is, in the capsule endoscope to which the technology of the LED-driving circuit disclosed in Japanese Unexamined Patent Application, First Publication No. 2002-319707 is applied, the signal lines corresponding to the number of the white LEDs+1 provided in the illumination unit passes through the second wiring substrate section, the imaging element substrate section and the first wiring substrate section.

The case in which the flexible substrate in which components that configure the capsule endoscope are mounted is provided in the capsule housing is considered. As described above, in the capsule endoscope, the wiring region of the flexible substrate, i.e., a portion of the first wiring substrate section and a portion of the second wiring substrate section are folded to be provided in the capsule housing. When the large number of signal lines pass through the first wiring substrate section and the second wiring substrate section by increasing the number of the white LEDs to achieve improvement in luminance (brightness) of the light irradiated onto the subject and uniformity of the illumination light, widths of the first wiring substrate section and the second wiring substrate section are increased according to the number of signals, and a region through which the wirings of the signals pass should be secured.

SUMMARY OF THE INVENTION

According to a first aspect of the present invention, a capsule endoscope includes a flexible substrate which is integrally formed by disposing an illumination substrate section, a first wiring substrate section, an imaging element substrate section, a second wiring substrate section, and a signal-processing substrate section in a row in sequence, the flexible substrate being accommodated in a capsule housing, wherein the imaging element substrate section is provided with an imaging element mounted on the imaging element substrate section and provided to output a pixel signal of a photographed subject, the imaging element including a plurality of pixels disposed in a two-dimensional matrix, the signal-processing substrate section is provided with a signal-processing unit mounted on the signal-processing substrate section, the signal-processing unit being provided to control photographing of the subject in the imaging element and generate an image by performing predetermined types of image processing to the pixel signal output from the imaging element, the illumination substrate section is provided with a plurality of light-emitting elements mounted on the illumination substrate, the plurality of light-emitting elements being included in an illumination unit provided to radiate light onto the photographed subject, the first wiring substrate section is provided such that wirings for signals passing between the illumination substrate section and the imaging element substrate section are formed, and the second wiring substrate section is provided such that wirings for signals passing between the imaging element substrate section and the signal-processing substrate section are formed; and an illumination control circuit which includes an illumination control signal output unit provided to output an illumination control signal to control light emission of the plurality of light-emitting elements provided in the illumination unit, and an illumination driving unit provided to drive the light-emitting elements according to the illumination control signal input from the illumination control signal output unit, wherein the light-emitting elements are LEDs, wherein the illumination driving unit is disposed on the imaging element substrate section or the illumination substrate section, and wherein the illumination driving unit includes a transistor array which is formed by a plurality of transistors, the plurality of transistors corresponding to each of the light-emitting elements provided in the illumination unit and generating illumination currents in accordance with the illumination control signal.

According to a second aspect of the present invention, in the capsule endoscope according to the first aspect, the illumination control signal output unit may include a voltage-current conversion circuit which is provided to convert a reference voltage into a current; and a control transistor which is provided to form the voltage-current conversion circuit and output a voltage signal generated in accordance with a value of the converted current as the illumination control signal, and the illumination driving unit may be configured such that each of the transistors in the transistor array is configured as a driving transistor which is provided to drive the corresponding light-emitting element, and each of the driving transistors generates the illumination current in accordance with a voltage value of the illumination control signal input into gate terminals.

According to a third aspect of the present invention, in the capsule endoscope according to the first aspect, the illumination control signal output unit may include a voltage-current conversion circuit which is provided to convert a reference voltage into a current; and a first current mirror circuit which is provided to output a signal of the current in which a value of the current converted by the voltage-current conversion circuit is reproduced as the illumination control signal, and the illumination driving unit may include a plurality of second current mirror circuits corresponding to each of the light-emitting elements, the plurality of second current mirror circuits generating the illumination current obtained by reproducing the value of the current of the illumination control signal by each of the transistors in the transistor array, and the illumination control signal being output from the first current mirror circuit.

According to a fourth aspect of the present invention, in the capsule endoscope according to the first aspect, the illumination control signal output unit may include an amplifier circuit configured to output a signal of a voltage according to a reference voltage as the illumination control signal, the illumination driving unit may further include a resistor array provided with a plurality of resistors corresponding to the transistors in the transistor array and connected to a reference potential of the amplifier circuit, and each of the transistors in the transistor array may be configured as a driving transistor provided to drive the corresponding light-emitting element, and each of the driving transistors is provided to generate the illumination current in accordance with a potential difference between a potential of the illumination control signal input into a gate terminal and a reference potential connected via the corresponding resistor in the resistor array.

According to a fifth aspect of the present invention, in the capsule endoscope according to any one of the second aspect to the fourth aspect, the illumination control signal output unit may include an operational amplifier configured to perform comparison of a voltage value of the reference voltage and a voltage value representing the illumination control signal.

According to a sixth aspect of the present invention, in the capsule endoscope according to any one of the first aspect to the fifth aspect, the illumination driving unit may be disposed on the imaging element substrate section, and the illumination driving unit may be formed as a component provided in the imaging element mounted on the imaging element substrate section.

BRIEF DESCRIPTION OF DRAWINGS

FIG. 13 is a view showing disposition and wiring of the illumination control circuit of the third configuration of the second embodiment.

DETAILED DESCRIPTION OF THE INVENTION

Figure 1A:
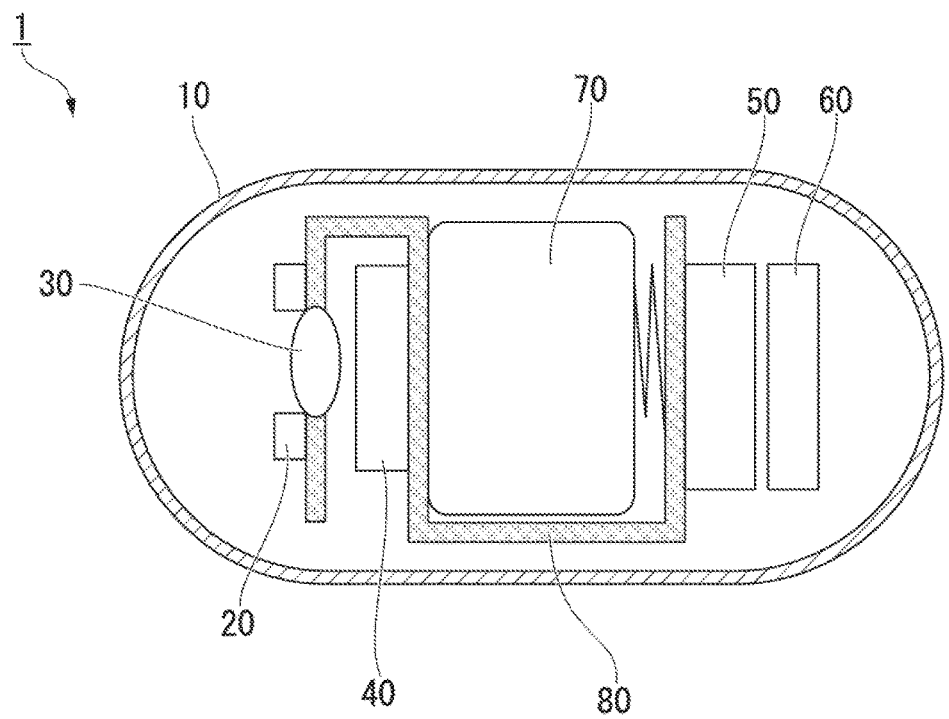
FIG. 1A is a view showing a structure of a capsule endoscope according to an embodiment of the present invention.
Figure 1B:
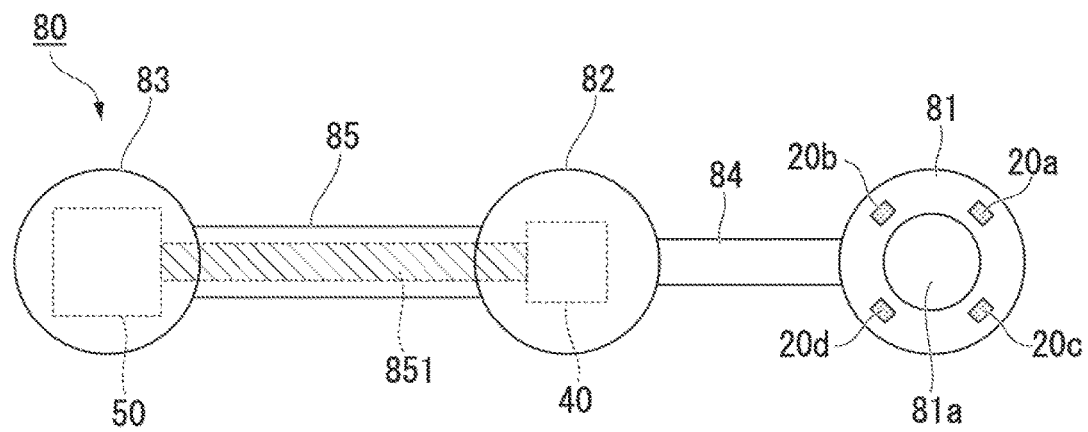
FIG. 1B is a view showing a structure of a flexible substrate in which components of the capsule endoscope according to the embodiment of the present invention are mounted.

Hereinafter, an embodiment of the present invention will be described with reference to the accompanying drawings. FIGS. 1A and 1B are views showing a configuration of a capsule endoscope according to the embodiment. FIG. 1A shows a structure in which components that configure a system of the capsule endoscope of the embodiment are provided in a capsule housing. FIG. 1B shows a structure of a flexible substrate in which the components that configure the capsule endoscope of the embodiment are mounted.

A capsule endoscope 1 shown in FIG. 1A includes an illumination unit 20, an optical system 30, an imaging element 40, a signal-processing unit 50, a communication antenna 60 and a power supply 70, which serve as a system of an endoscope. Also, in the capsule endoscope 1, components that configure the endoscope are provided in a capsule housing 10 while being mounted on a flexible substrate 80. More specifically, the components that configure the endoscope are provided from one end of the capsule housing 10 in sequence of the illumination unit 20, the optical system 30, the imaging element 40, the power supply 70, the signal-processing unit 50 and the communication antenna 60.

The capsule endoscope 1 photographs the subject using the imaging element 40, processes the photographed image (for example, a still image or the like) or video (for example, moving pictures or the like) using the signal-processing unit 50, and transmits the image or video to the outside through wireless communication. In the following description, the image or the video is referred to as "an image" without distinction.

The capsule housing 10 is a tubular housing having end portions formed in hemispherical shapes and configured to accommodate the components of the capsule endoscope 1. An end of the capsule housing 10 in which the illumination unit 20, the optical system 30 and the imaging element 40 are provided is formed of a transparent material.

The illumination unit 20 includes a plurality of light-emitting elements such as white LEDs or the like, and radiates light onto the photographed subject when photographing of the subject is performed by the capsule endoscope 1. Further, in the following description, the case in which the light-emitting elements provided in the illumination unit 20 are white LEDs will be described.

The optical system 30 is provided by an optical lens and so on configured to collect subject light from the subject onto which light is irradiated by the illumination unit 20. The optical system 30 forms an optical image of the subject photographed by the capsule endoscope 1 on an imaging surface of the imaging element 40.

The imaging element 40 is a charge-coupled device (CCD) image sensor configured to photoelectrically convert the optical image of the subject imaged on the imaging surface by the optical system 30, or a solid state imaging device represented by a complementary metal-oxide semiconductor (CMOS) image sensor. The imaging element 40 includes a plurality of pixels disposed in a two-dimensional matrix shape, photographs the subject according to a control signal input from the signal-processing unit 50, and outputs the pixel signals of the photographed subject to the signal-processing unit 50.

The signal-processing unit 50 transmits the image of the subject generated based on the pixel signals input from the imaging element 40 to the outside of the capsule endoscope 1 through wireless communication. More specifically, the signal-processing unit 50 performs predetermined various types of image processing to generate the image of the subject with respect to the pixel signals input from the imaging element 40. Then, the signal-processing unit 50 transmits data of the generated image of the subject (hereinafter, referred to as "image data") to the outside of the capsule endoscope 1 through wireless communication using the communication antenna 60. In addition, the signal-processing unit 50 performs control of the entire capsule endoscope 1 such as photographing control in the capsule endoscope 1, control of the luminance (brightness) of the light irradiated onto the subject, or the like. Further, the control of the entire capsule endoscope 1 by the signal-processing unit 50 may be performed according to an instruction transmitted from the outside of the capsule endoscope 1 through wireless communication.

The power supply 70 supplies power required for the components provided in the capsule endoscope 1. The communication antenna 60 performs transmission and reception of the wireless signals when the signal-processing unit 50 performs wireless communication between the signal-processing unit 50 and the outside of the capsule endoscope 1.

In the capsule endoscope 1, the components of the above-mentioned system configuration are mounted on the flexible substrate 80 having the shape as shown in FIG. 1B. The flexible substrate 80 shown in FIG. 1B includes a component mounting region and a wiring region. The component mounting region has an illumination substrate section 81, an imaging element substrate section 82 and a signal-processing substrate section 83. The wiring region has a first wiring substrate section 84 and a second wiring substrate section 85. Then, as shown in FIG. 1B, the flexible substrate 80 is integrally formed in a shape in which the substrate sections are arranged in a row in sequence of the illumination substrate section 81, the first wiring substrate section 84, the imaging element substrate section 82, the second wiring substrate section 85 and the signal-processing substrate section 83.

The illumination substrate section 81 is the component mounting region in which the plurality of white LEDs provided in the illumination unit 20 are mounted. FIG. 1B shows a state in which four white LEDs 20a to 20d provided in the illumination unit 20 are mounted in the surface of the illumination substrate section 81 at predetermined intervals. Further, as shown in FIG. 1B, the illumination substrate section 81 is formed in a doughnut shape having an opening section 81a formed in a center thereof. The opening section 81a is a window configured to guide the subject light to the imaging surface of the imaging element 40 in a state in which the components that configure the endoscope are provided in the capsule housing 10. The optical system 30 configured to collect the subject light to form the optical image of the subject on the imaging surface of the imaging element 40 is disposed at a position of the opening section 81a.

The imaging element substrate section 82 is the component mounting region on which the imaging element 40 is mounted. FIG. 1B shows a state in which the imaging element 40 is mounted on a back surface of the imaging element substrate section 82.

The signal-processing substrate section 83 is the component mounting region on which the signal-processing unit 50 is mounted. FIG. 1B shows a state in which the signal-processing unit 50 is mounted on the back surface of the signal-processing substrate section 83.

The first wiring substrate section 84 is the wiring region in which the wirings of the signals passing between the illumination substrate section 81 and the imaging element substrate section 82 are formed. The wirings of the signals transmitted and received between the components provided in the illumination unit 20 and the signal-processing unit 50 or the imaging element 40 are formed at the first wiring substrate section 84. The components provided in the illumination unit 20 and the signal-processing unit 50 or the imaging element 40 are electrically connected by the wirings formed at the first wiring substrate section 84.

The second wiring substrate section 85 is the wiring region in which the wirings of the signals passing between the imaging element substrate section 82 and the signal-processing substrate section 83 are formed. The wirings of the signals transmitted and received between the imaging element 40 and the signal-processing unit 50 are formed at the second wiring substrate section 85. The imaging element 40 and the signal-processing unit 50 are electrically connected by the wirings formed at the second wiring substrate section 85. Further, in the capsule endoscope 1, since the large number of signals such as control signals, pixel signals, or the like, related to the photographing are transmitted and received between the imaging element 40 and the signal-processing unit 50, the number of the wirings formed at the second wiring substrate section 85 is increased. In FIG. 1B, the wirings of the signals transmitted and received between the imaging element 40 and the signal-processing unit 50 are shown as the wiring group 851.

In the capsule endoscope 1, the flexible substrate 80 on which the components that configure the endoscope are mounted or disposed is provided in the capsule housing 10 in a state in which the flexible substrate 80 is folded as shown in FIG. 1A. Further, in FIG. 1A, while the case in which the signal-processing unit 50 and the communication antenna 60 are sequentially provided is shown, the signal-processing unit 50 and the communication antenna 60 may be provided in parallel, i.e., side by side in a depth direction of FIG. 1A. In this case, the communication antenna 60 is mounted on the signal-processing substrate section 83. In addition, in FIG. 1A, the power supply 70 is disposed on the flexible substrate 80 in the folded state between the imaging element substrate section 82 and the signal-processing substrate section 83. Accordingly, for example, contact members that come in contact with terminals (poles) of the power supply 70 are mounted on surfaces of the imaging element substrate section 82 and the signal-processing substrate section 83.

<First Embodiment>

Next, in the capsule endoscope 1 of the embodiment, the illumination control circuit configured to control light emission of the white LEDs provided in the illumination unit 20 will be described.

<First Configuration>

Figure 2:
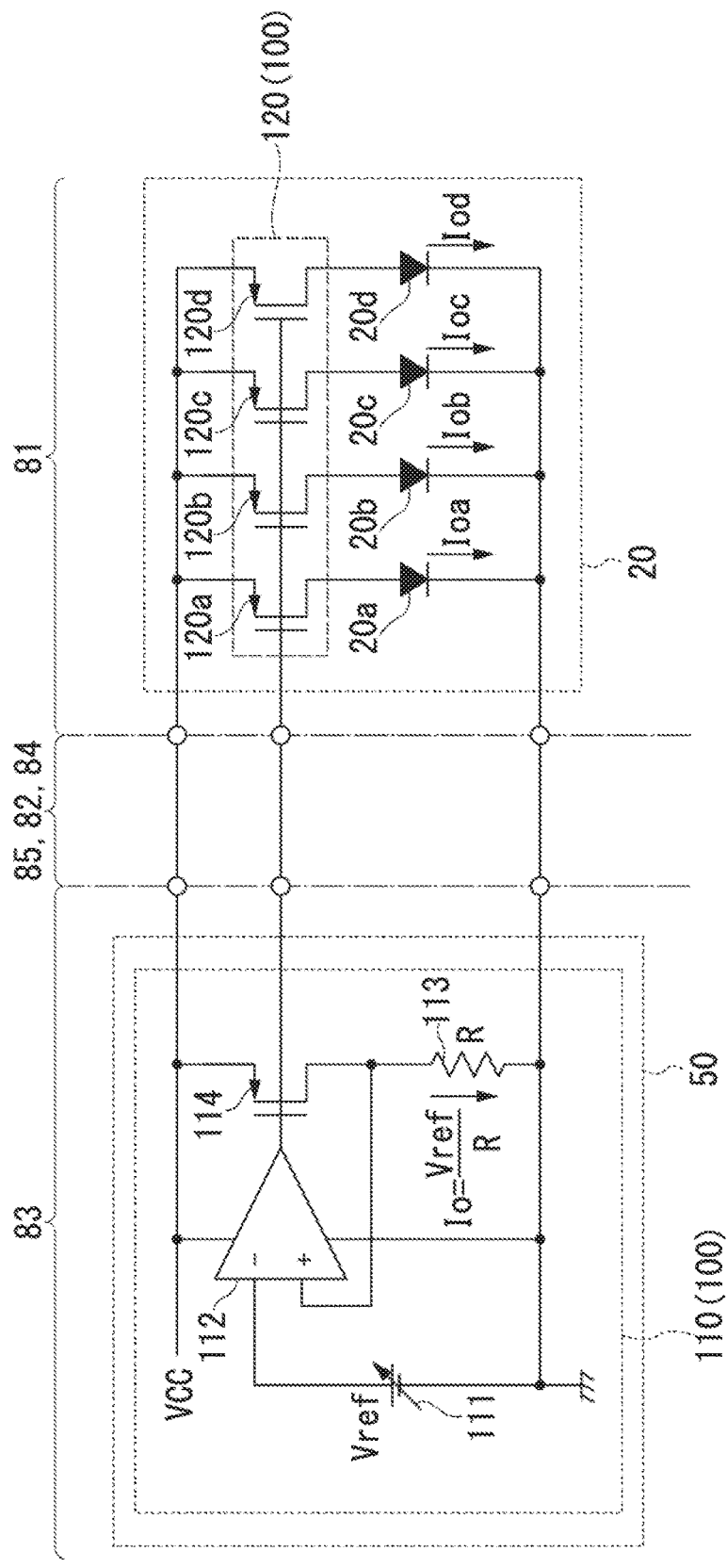
FIG. 2 is a circuit diagram showing a first configuration of an illumination control circuit of the first embodiment of the present invention.

First, a first configuration of the illumination control circuit of the first embodiment will be described. FIG. 2 is a circuit diagram showing the first configuration of the illumination control circuit of the first embodiment. An illumination control circuit 100 of the first configuration shown in FIG. 2 is provided by an illumination control signal output unit 110 and an illumination driving unit 120. In the illumination control circuit 100 of the first configuration, the illumination control signal output unit 110 is disposed in the signal-processing unit 50 mounted on the signal-processing substrate section 83, and the illumination driving unit 120 is disposed together with the illumination unit 20 mounted on the illumination substrate section 81.

The illumination control signal output unit 110 outputs an illumination control signal for controlling the driving of the white LEDs provided in the illumination unit 20 using the illumination driving unit 120, and controls the luminance (brightness) of the light emitted from the white LEDs. The illumination driving unit 120 directly drives the white LEDs provided in the illumination unit 20 according to the illumination control signal input from the illumination control signal output unit 110. In the illumination control circuit 100 of the first configuration, a transistor array is provided as the illumination driving unit 120. In the following description, the illumination driving unit 120 will be described as a transistor array 120.

The illumination control signal output unit 110 is provided by a reference power supply 111, an operational amplifier 112, a resistor 113 and a control transistor 114. The reference power supply 111 is a power supply configured to output a changeable reference voltage (hereinafter, referred to as "a reference voltage Vref"). The reference power supply 111 has a positive terminal that is connected to an inverting input terminal of the operational amplifier 112, and a negative terminal that is connected to the ground. The operational amplifier 112 is the operational amplifier. In the operational amplifier 112, the inverting input terminal is connected to the positive terminal of the reference power supply 111, a non-inverting input terminal is connected to one terminal of the resistor 113, and the output terminal is connected to a gate terminal of the control transistor 114. The reference voltage Vref is input into the inverting input terminal of the operational amplifier 112, and the voltage of the one terminal of the resistor 113, i.e., the reference voltage Vref appears at the non-inverting input terminal by a virtual short of the operational amplifier 112. The resistor 113 is a resistor having a predetermined resistance value R. The resistor 113 has one terminal that is connected to the non-inverting input terminal of the operational amplifier 112, and the other terminal that is connected to the ground.

The control transistor 114 has a gate terminal that is connected to the output terminal of the operational amplifier 112, a source terminal that is connected to a power supply voltage VCC, and a drain terminal that is connected to the one terminal of the resistor 113 and the non-inverting input terminal of the operational amplifier 112. In addition, the gate terminal of the control transistor 114 is also connected to the gate terminals of the transistors provided in the transistor array 120. The illumination control signal output unit 110 is operated as the voltage-current conversion circuit by a configuration of the reference power supply 111, the operational amplifier 112, the resistor 113 and the control transistor 114.

The transistor array 120 is provided by a plurality of driving transistors disposed in an array and having the same transistor size. FIG. 2 shows the transistor array 120 including four driving transistors 120a to 120d. Further, the control transistor 114 provided in the illumination control signal output unit 110 and the driving transistors 120a to 120d in the transistor array 120 have the same transistor size. The driving transistors 120a to 120d provided in the transistor array 120 correspond to the four white LEDs 20a to 20d provided in the illumination unit 20, respectively. Then, the driving transistors 120a to 120d drive the corresponding white LEDs 20a to 20d, respectively.

The driving transistors 120a to 120d have gate terminals connected to the gate terminal of the control transistor 114 and the output terminal of the operational amplifier 112, source terminals connected to the power supply voltage VCC, and drain terminals connected to anode terminals of the corresponding white LEDs 20a to 20d. Further, the cathode terminals of the white LEDs 20a to 20d are connected to the ground.

Next, an operation of the illumination control circuit 100 of the first configuration of the first embodiment will be described. In the illumination control circuit 100 of the first configuration of the first embodiment, the voltage-current conversion circuit of the illumination control signal output unit 110 provided by the reference power supply 111, the operational amplifier 112, the resistor 113 and the control transistor 114 generates an output current of a current value Io=Vref/R including the reference voltage Vref appearing at the non-inverting input terminal of the operational amplifier 112 by a virtual short of the operational amplifier 112 and according to the resistance value R of the resistor 113, based on the reference voltage Vref output by the reference power supply 111. Accordingly, the control transistor 114 generates a voltage according to the current value Io flowing to the drain terminal (hereinafter, referred to as "a gate control voltage VGS") between the gate terminal and the source terminal. Then, the generated voltage signal of the gate control voltage VGS is output from the voltage output terminal of the illumination control signal output unit 110. In the illumination control circuit 100 of the first configuration, the voltage signal of the gate control voltage VGS output from the voltage output terminal of the illumination control signal output unit 110 is the illumination control signal.

Here, the voltage signal of the gate control voltage VGS generated by the control transistor 114 is input into the voltage input terminal of the transistor array 120 disposed on the illumination substrate section 81 and input into the gate terminals of the driving transistors 120a to 120d in the transistor array 120 via the second wiring substrate section 85, the imaging element substrate section 82 and the first wiring substrate section 84. Further, in the illumination control circuit 100, the power supply voltage VCC and the ground are also shared by the components in the illumination control circuit 100 and the illumination unit 20. The voltage signal of the power supply voltage VCC and the voltage signal of the ground are also input into the illumination substrate section 81 via the second wiring substrate section 85, the imaging element substrate section 82 and the first wiring substrate section 84.

The driving transistors 120a to 120d generates the same output current (hereinafter, referred to as "an illumination current") of the current value Io as that of the voltage-current conversion circuit flowing from the source terminal to the drain terminal according to a potential difference between the gate control voltage VGS input into the gate terminal and the power supply voltage VCC input into the source terminal, i.e., a voltage between the gate terminal and the source terminal.

Then, the illumination currents generated by the driving transistors 120a to 120d flow to the corresponding white LEDs 20a to 20d, respectively. More specifically, as shown in FIG. 2, an illumination current of a current value Ioa generated by the driving transistor 120a flows to the corresponding white LED 20a, an illumination current of a current value Iob generated by the driving transistor 120b flows to the corresponding white LED 20b, an illumination current of a current value Ioc generated by the driving transistor 120c flows to the corresponding white LED 20c, and an illumination current of a current value Iod generated by the driving transistor 120d flows to the corresponding white LED 20d.

Accordingly, the white LEDs 20a to 20d emit light with the luminance (brightness) according to the current value of the flowed illumination current.

Further, in the illumination control circuit 100, as the voltage value of the reference voltage Vref output from the reference power supply 111 is varied, the current value Io of the generated output current can be changed, and the voltage value of the gate control voltage VGS can be changed. That is, in the illumination control circuit 100, as the voltage value of the reference voltage Vref output by the reference power supply 111 is varied, the current values Ioa to Iod of the illumination current flowing through the white LEDs 20a to 20d can be controlled, and the luminance (brightness) of the light emitted from the white LEDs 20a to 20d can be controlled.

Figure 3:
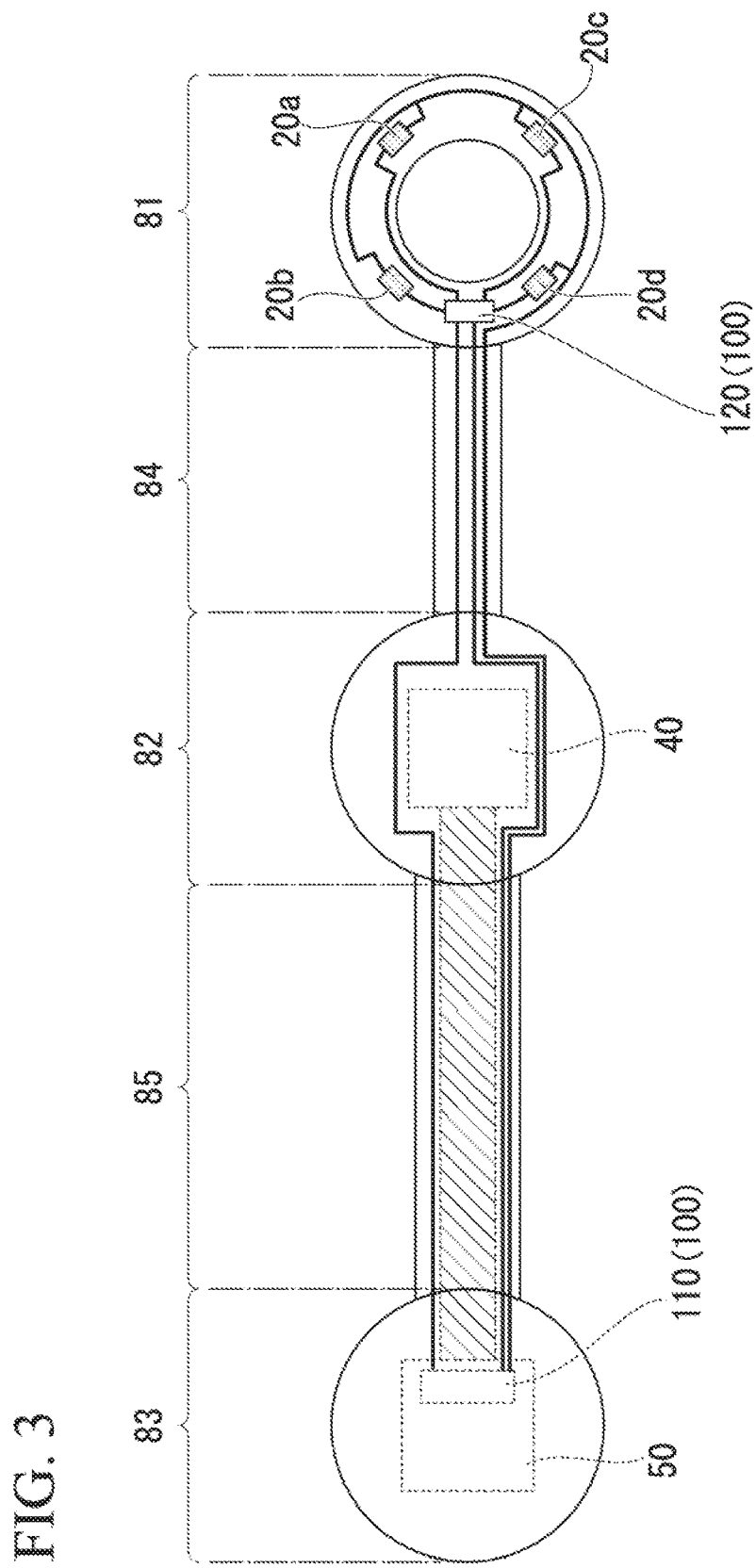
FIG. 3 is a view showing disposition and wiring of the illumination control circuit of the first configuration of the first embodiment.

Next, disposition of the components in the illumination control circuit 100 of the first configuration of the first embodiment and the wirings in the flexible substrate 80 between the components provided in the illumination control circuit 100 will be described. FIG. 3 is a view showing disposition and wirings of the illumination control circuit 100 of the first configuration of the first embodiment. FIG. 3 shows the case in which the components of the illumination control circuit 100 are disposed on the flexible substrate 80 having the shape shown in FIG. 1B.

As described above, the illumination control signal output unit 110 that configures the illumination control circuit 100 is disposed in the signal-processing unit 50 mounted on the signal-processing substrate section 83, and the transistor array 120 is disposed together with the illumination unit 20 mounted on the illumination substrate section 81. Then, in the illumination control circuit 100, the voltage signal (the illumination control signal) of the gate control voltage VGS connected between the illumination control signal output unit 110 and the transistor array 120, and the voltage signal of the power supply voltage VCC and the voltage signal of the ground are connected via the second wiring substrate section 85, the imaging element substrate section 82 and the first wiring substrate section 84. That is, as shown in FIG. 3, in the illumination control circuit 100, three wirings pass through the second wiring substrate section 85, the imaging element substrate section 82 and the first wiring substrate section 84.

According to the first configuration of the first embodiment, a capsule endoscope (a capsule endoscope 1) is provided having an imaging element substrate section (an imaging element substrate section 82) including a plurality of pixels disposed in a two-dimensional matrix shape and on which an imaging element (an imaging element 40) configured to output a pixel signal of a photographed subject is mounted, a signal-processing substrate section (a signal-processing substrate section 83) configured to control photographing of the subject in the imaging element 40 and on which a signal-processing unit (a signal-processing unit 50) configured to generate an image on which predetermined types of image processing are performed with respect to the pixel signal output from the imaging element 40 is mounted, an illumination substrate section (a illumination substrate section 81) on which a plurality of light-emitting elements (white LEDs 20a to 20d) provided in an illumination unit (an illumination unit 20) configured to radiate light onto the photographed subject are mounted, a first wiring substrate section (a first wiring substrate section 84) in which wirings of signals passing between the illumination substrate section 81 and the imaging element substrate section 82 are formed, and a second wiring substrate section (a second wiring substrate section 85) in which wirings of signals passing between the imaging element substrate section 82 and the signal-processing substrate section 83 are formed, a flexible substrate (a flexible substrate 80) integrally formed in a shape in which the substrate sections are arranged in a row in sequence of the illumination substrate section 81, the first wiring substrate section 84, the imaging element substrate section 82, the second wiring substrate section 85 and the signal-processing substrate section 83 being provided in a capsule housing (a capsule housing 10), the capsule endoscope 1 including: an illumination control circuit (an illumination control circuit 100) having an illumination control signal output unit (an illumination control signal output unit 110) configured to output an illumination control signal to control light emission of the plurality of light-emitting elements (the white LEDs 20a to 20d) provided in the illumination unit 20, and an illumination driving unit (an illumination driving unit 120) configured to drive the white LEDs 20a to 20d according to the illumination control signal input from the illumination control signal output unit 110, wherein the illumination driving unit 120 is disposed on either the imaging element substrate section 82 or the illumination substrate section 81.

In addition, according to the first configuration of the first embodiment, the capsule endoscope 1 is provided in which the white LEDs 20a to 20d are LEDs, and the illumination driving unit 120 includes a transistor array (a transistor array 120) corresponding to the plurality of light-emitting elements (the white LEDs 20a to 20d) provided in the illumination unit 20 and including a plurality of transistors configured to generate an illumination current according to the illumination control signal.

In addition, according to the first configuration of the first embodiment, the capsule endoscope 1 is provided in which the illumination control signal output unit 110 includes a voltage-current conversion circuit (provided by a reference power supply 111, an operational amplifier 112, a resistor 113 and a control transistor 114) configured to convert a reference voltage (a reference voltage Vref) into a current, and the control transistor (a control transistor 114) that configures the voltage-current conversion circuit and in which the converted current is input into a drain terminal, and the signal of the voltage generated according to the input current value is output as the illumination control signal, and the transistors in the transistor array 120 in the illumination driving unit 120 are configured as driving transistors (driving transistors 120a to 120d) configured to drive the corresponding white LEDs 20a to 20d, and the driving transistors 120a to 120d generate illumination currents according to the voltage values of the illumination control signals input into gate terminals.

In addition, according to the first configuration of the first embodiment, the capsule endoscope 1 is provided in which the illumination control signal output unit 110 includes the operational amplifier (the operational amplifier 112) configured to perform comparison of a voltage value of the reference voltage Vref and a voltage value representing the illumination control signal.

According to the above-mentioned configuration, operation and disposition, the illumination control circuit 100 controls light emission of the white LEDs 20a to 20d provided in the illumination unit 20 of the capsule endoscope 1. Here, in the illumination control circuit 100, the current values Ioa to Iod of the illumination current flowing through the white LEDs 20a to 20d are the same current value as the current value Io of the output current generated by the voltage-current conversion circuit in the illumination control signal output unit 110. In the illumination control circuit 100, the white LEDs 20a to 20d can uniformly emit light without deviation of the luminance (brightness) of the light emitted from the white LEDs 20a to 20d. Then, as the illumination control circuit 100 is used as the illumination control circuit configured to control light emission of the white LEDs 20a to 20d provided in the illumination unit 20 of the capsule endoscope 1, performance (brightness) or quality (uniformity of illumination light) of the illumination unit 20 obtained by the capsule endoscope 1 can be easily secured.

In addition, in the illumination control circuit 100, light emission of the white LEDs 20a to 20d provided in the illumination unit 20 can be controlled with a number of wirings (the number of signal lines) smaller than the number of LEDs+1 in the related art. When the illumination control circuit 100 is used as the illumination control circuit configured to control light emission of the white LEDs 20a to 20d provided in the illumination unit 20 of the capsule endoscope 1, light emission of the white LEDs 20a to 20d can be controlled without increasing the widths of the second wiring substrate section 85 and the first wiring substrate section 84 very much. Accordingly, the illumination control circuit 100 can be easily applied to the capsule endoscope 1 without necessity of review of the method of passing the wiring through, which was needed in the related art.

Further, in the illumination control circuit 100, as described above, the control transistor 114 provided in the illumination control signal output unit 110 and the driving transistors 120a to 120d in the transistor array 120 have the same transistor size. However, the control transistor 114 and the driving transistors 120a to 120d are disposed at separated positions. An error may occur in the current value Io of the output current generated by the voltage-current conversion circuit in the illumination control signal output unit 110 and the current values Ioa to Iod of the illumination currents generated by the driving transistors 120a to 120d, i.e., the current values Ioa to Iod of the illumination current flowing to the white LEDs 20a to 20d. In the illumination control circuit 100, as described above, the driving transistors 120a to 120d in the transistor array 120 have the same transistor size. In the transistor array 120, similarly, the current values Ioa to Iod of the illumination current generated according to the gate control voltage VGS and the power supply voltage VCC have the same current value. Accordingly, in the illumination control circuit 100, as the control transistor 114 and the driving transistors 120a to 120d are disposed at separated positions, even when errors occurs between the current value Io of the output current and the current values Ioa to Iod of the illumination currents, the current values of the illumination currents flowing to the white LEDs have the same current value, and a deviation does not occur in the luminance (brightness) of the light emitted from the white LEDs 20a to 20d.

In addition, in the illumination control circuit 100, light emission of a larger number of white LEDs can be controlled by only using the transistor array 120 corresponding to the white LEDs provided in the illumination unit 20. That is, in the illumination control circuit 100, the number of the wirings connected between the illumination control signal output unit 110 and the transistor array 120 is not influenced by the number of the white LEDs provided in the illumination unit 20, and light emission of all of the white LEDs provided in the illumination unit 20 can be uniformly controlled by three wirings.

Further, in the illumination control circuit 100, the driving transistors 120a to 120d provided in the transistor array 120 are the transistors disposed in an array and having the same transistor size. It is considered that properties of the driving transistors 120a to 120d provided in the transistor array 120 are the same property, i.e., matched to each other. However, from a relation of mounting the plurality of white LEDs on the illumination substrate section 81, the transistor array 120 in which the driving transistors 120a to 120d are disposed in an array may not be mounted on the illumination substrate section 81. In this case, it is considered that the driving transistors 120a to 120d provided in the transistor array 120 are provided by individual transistors. However, even in this case, for example, as the same lot of transistors are employed or the transistors having the same property are selected, it is preferable to match properties of the driving transistors 120a to 120d provided in the transistor array 120.

In addition, in the illumination control circuit 100, the control transistor 114 provided in the illumination control signal output unit 110 and the driving transistors 120a to 120d in the transistor array 120 also have the same transistor size. Furthermore, it is preferable to match properties of the control transistor 114 and the driving transistors 120a to 120d. It is considered that the signal-processing unit 50 in which the control transistor 114 is disposed and the transistor array 120 are formed by manufacturing a plurality of types of semiconductor chips in the same lot using a method of manufacturing a semiconductor device, for example, which is referred to as a multi-shot. However, as described above, in the illumination control circuit 100, as the control transistor 114 and the driving transistors 120a to 120d are disposed at separated positions, even when an error occurs in the current value Io of the output current and the current values Ioa to Iod of the illumination current, no deviation in luminance (brightness) of the light emitted from the white LEDs 20a to 20d occurs. That is, even when the control transistor 114 and the transistor array 120 are not completely matched with each other, performance (brightness) or quality (uniformity of illumination light) of the illumination unit 20 obtained by the capsule endoscope 1 can be secured. It is also considered that properties of the control transistor 114 and the driving transistors 120a to 120d may be deviated as long as the deviation is within a certain range.

<Second Configuration>

Figure 4:
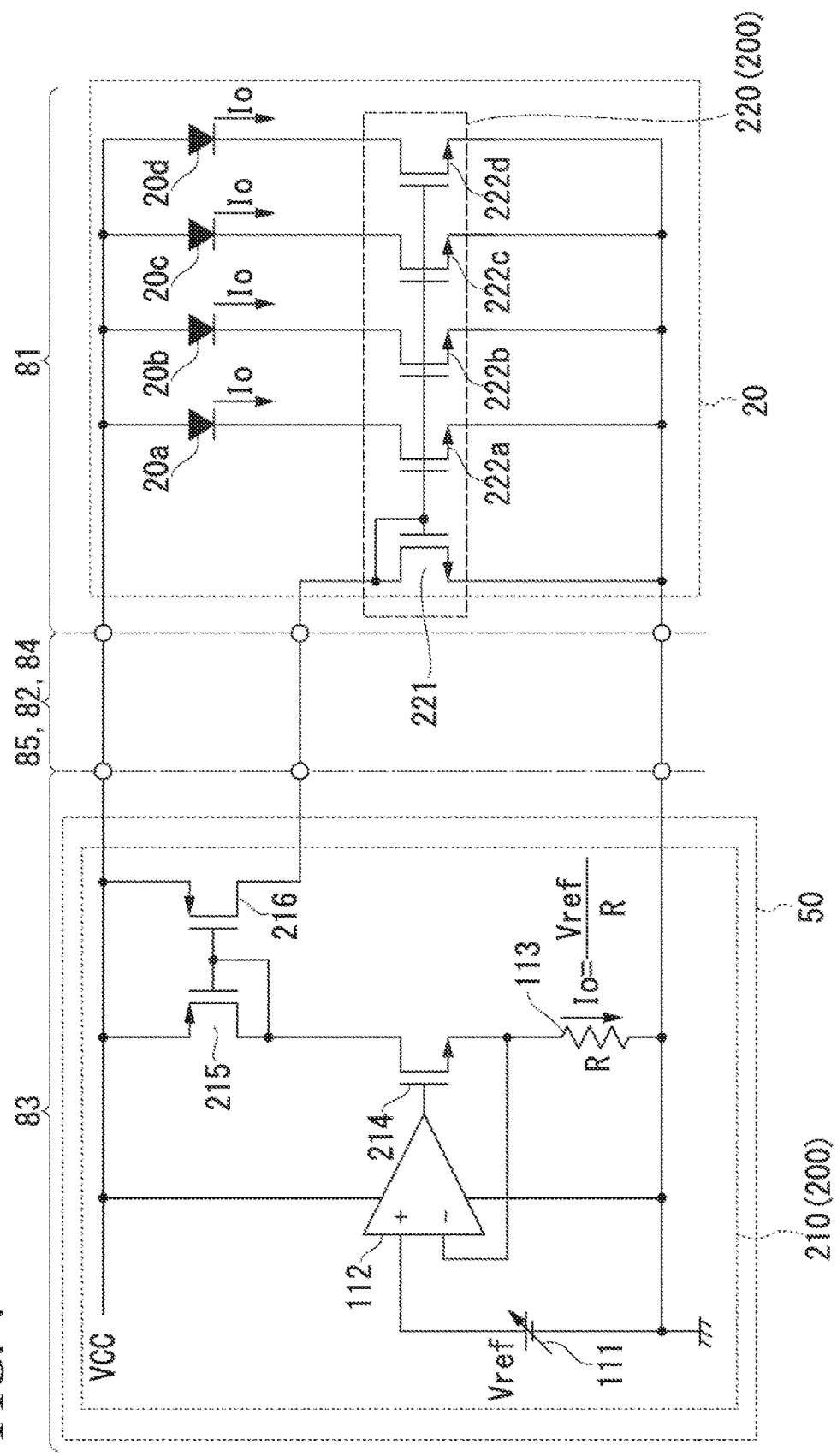
FIG. 4 is a circuit diagram showing a second configuration of the illumination control circuit of the first embodiment.

Next, a second configuration of the illumination control circuit of the first embodiment will be described. FIG. 4 is a circuit diagram showing the second configuration of the illumination control circuit of the first embodiment. An illumination control circuit 200 of the second configuration shown in FIG. 4 is provided by an illumination control signal output unit 210 and an illumination driving unit 220. In the illumination control circuit 200 of the second configuration, similar to the illumination control circuit 100 of the first configuration, the illumination control signal output unit 210 is disposed in the signal-processing unit 50 mounted on the signal-processing substrate section 83, and the illumination driving unit 220 is disposed together with the illumination unit 20 mounted on the illumination substrate section 81. Further, the same components as those of the illumination control circuit 100 of the first configuration are also included in the components of the illumination control circuit 200 of the second configuration. Accordingly, in the components of the illumination control circuit 200 of the second configuration, the same reference numerals designates the same components as those of the illumination control circuit 100 of the first configuration, and detailed description of the components will be omitted.

Like the illumination control circuit 100 of the first configuration, the illumination control signal output unit 210 outputs the illumination control signal for controlling driving of the white LEDs provided in the illumination unit 20 using the illumination driving unit 220, and controls luminance (brightness) of the light emitted from the white LEDs. The illumination driving unit 220 directly drives the white LEDs provided in the illumination unit 20 according to the illumination control signal input from the illumination control signal output unit 210. In the illumination control circuit 200 of the second configuration, the transistor array is provided as the illumination driving unit 220. In the following description, the illumination driving unit 220 will be described as a transistor array 220.

The illumination control signal output unit 210 is provided by a reference power supply 111, an operational amplifier 112, a resistor 113, a transistor 214, a first input-side transistor 215 and a first output-side transistor 216. The reference power supply 111, the operational amplifier 112 and the resistor 113 are the same components as those of the illumination control circuit 100 of the first configuration. However, in the illumination control signal output unit 210, a positive terminal of the reference power supply 111 is connected to a non-inverting input terminal of the operational amplifier 112, and one terminal of the resistor 113 and a source terminal of the transistor 214 are connected to an inverting input terminal, and a gate terminal of the transistor 214 is connected to an output terminal. A reference voltage Vref is input into the non-inverting input terminal of the operational amplifier 112, a voltage of the one terminal of the resistor 113, i.e., the reference voltage Vref appears at the inverting input terminal by a virtual short of the operational amplifier 112.

The transistor 214 has a gate terminal that is connected to an output terminal of the operational amplifier 112, a drain terminal that is connected to a drain terminal of the first input-side transistor 215, and a source terminal that is connected to the one terminal of the resistor 113 and the inverting input terminal of the operational amplifier 112. Similar to the illumination control circuit 100 of the first configuration, the illumination control signal output unit 210 is also operated as a voltage-current conversion circuit by a configuration of the reference power supply 111, the operational amplifier 112, the resistor 113 and the transistor 214.

In addition, in the illumination control signal output unit 210, a first current mirror circuit is provided by the first input-side transistor 215 and the first output-side transistor 216. Further, the first input-side transistor 215 and the first output-side transistor 216 that configure the first current mirror circuit have the same transistor size and matched properties. The first input-side transistor 215 has a gate terminal that is connected to the drain terminal and the gate terminal of the first output-side transistor 216, a source terminal that is connected to the power supply voltage VCC, and a drain terminal connected to the drain terminal of the transistor 214. The first output-side transistor 216 has a gate terminal that is connected to the gate terminal of the first input-side transistor 215, a source terminal that is connected to the power supply voltage VCC, and a drain terminal that is connected to the current output terminal of the illumination control signal output unit 210. Also, the drain terminal of the first output-side transistor 216 is connected to the current input terminal of the second current mirror circuit provided in the transistor array 220.

The transistor array 220 is provided by a second input-side transistor 221 and a plurality of second output-side transistors that are disposed in an array and have the same transistor size and matched properties. FIG. 4 shows the transistor array 220 including a second input-side transistor 221 and four second output-side transistors 222a to 222d.

In the transistor array 220 shown in FIG. 4, a second current mirror circuit corresponding to the white LED 20a provided in the illumination unit 20 is provided by the second input-side transistor 221 and the second output-side transistor 222a. In addition, a second current mirror circuit corresponding to the white LED 20b is provided by the second input-side transistor 221 and the second output-side transistor 222b, a second current mirror circuit corresponding to the white LED 20c is provided by the second input-side transistor 221 and the second output-side transistor 222c, and a second current mirror circuit corresponding to the white LED 20d is provided by the second input-side transistor 221 and the second output-side transistor 222d. Also, the second current mirror circuits drive the corresponding white LEDs 20a to 20d, respectively.

The second input-side transistor 221 has a gate terminal that is connected to the drain terminals and the gate terminals of the second output-side transistors 222a to 222d, a source terminal that is connected to the ground, and a drain terminal that is connected to the current input terminal of the transistor array 220. Also, the drain terminal of the second input-side transistor 221 is connected to the current output terminal of the first current mirror circuit provided in the illumination control signal output unit 210. The second output-side transistors 222a to 222d have gate terminals that are connected to the gate terminal of the second input-side transistor 221, source terminals that are connected to the ground, and drain terminals that are connected to cathode terminals of the corresponding white LEDs 20a to 20d. Further, anode terminals of the white LEDs 20a to 20d are connected to the power supply voltage VCC.

Next, an operation of the illumination control circuit 200 of the second configuration of the first embodiment will be described. Even in the illumination control circuit 200 of the second configuration of the first embodiment, like the illumination control circuit 100 of the first configuration, in the illumination control signal output unit 210, the voltage-current conversion circuit provided by the reference power supply 111, the operational amplifier 112, the resistor 113 and the transistor 214 generates the current of the current value Io=Vref/R including the reference voltage Vref appearing at the inverting input terminal of the operational amplifier 112 by a virtual short of the operational amplifier 112 and according to the resistance value R of the resistor 113, based on the reference voltage Vref output by the reference power supply 111. Then, the current of the current value Io generated by the voltage-current conversion circuit is reproduced by the first current mirror circuit provided by the first input-side transistor 215 and the first output-side transistor 216 of the illumination control signal output unit 210, and output from the current output terminal as the current signal of the current value Io. In the illumination control circuit 200 of the second configuration, the current signal of the current value Io reproduced by the first current mirror circuit provided by the illumination control signal output unit 210 and output from the current output terminal is an illumination control signal.

Here, the current signal of the current value Io reproduced by the first current mirror circuit is input into the current input terminal of the transistor array 220 disposed on the illumination substrate section 81 and input into the drain terminal and the gate terminal of the second input-side transistor 221 in the transistor array 220 via the second wiring substrate section 85, the imaging element substrate section 82 and the first wiring substrate section 84. Further, even in the illumination control circuit 200, like the illumination control circuit 100 of the first configuration, the power supply voltage VCC and the ground are also shared by the components in the illumination control circuit 200 and the illumination unit 20. Similar to the illumination control circuit 100 of the first configuration, the voltage signal of the power supply voltage VCC and the voltage signal of the ground are also input into the illumination substrate section 81 via the second wiring substrate section 85, the imaging element substrate section 82 and the first wiring substrate section 84.

Then, in the transistor array 220, the second current mirror circuits provided by the second input-side transistor 221 and the second output-side transistors 222a to 222d reproduce the current of the current value Io. Accordingly, the illumination current of the same current value Io as the input current, i.e., the same current value Io as the current formed by the voltage-current conversion circuit flows to the white LEDs 20a to 20d corresponding to the second current mirror circuit.

More specifically, as shown in FIG. 4, the illumination current of the current value Io reproduced by the second current mirror circuit provided by the second input-side transistor 221 and the second output-side transistor 222a flows to the corresponding white LED 20a provided in the illumination unit 20. In addition, the illumination current of the current value Io reproduced by the second current mirror circuit provided by the second input-side transistor 221 and the second output-side transistor 222b flows to the corresponding white LED 20b provided in the illumination unit 20. In addition, the illumination current of the current value Io reproduced by the second current mirror circuit provided by the second input-side transistor 221 and the second output-side transistor 222c flows to the corresponding white LED 20c provided in the illumination unit 20, and the illumination current of the current value Io reproduced by the second current mirror circuit provided by the second input-side transistor 221 and the second output-side transistor 222d flows to the corresponding white LED 20d provided in the illumination unit 20.

Accordingly, the white LEDs 20a to 20d emit light with the luminance (brightness) according to the current value Io of the flowed illumination current.

Further, even in the illumination control circuit 200, like the illumination control circuit 100 of the first configuration, as the voltage value of the reference voltage Vref output by the reference power supply 111 is varied, the current value Io of the generated output current can be changed, and reproduced by the first current mirror circuit, and the current value Io of the current generated by the voltage-current conversion circuit can be changed. Accordingly, even in the illumination control circuit 200, like the illumination control circuit 100 of the first configuration, the current value Io of the illumination current flowing to the white LEDs 20a to 20d can be controlled, and the luminance (brightness) of the light emitted from the white LEDs 20a to 20d can be controlled.

Figure 5:
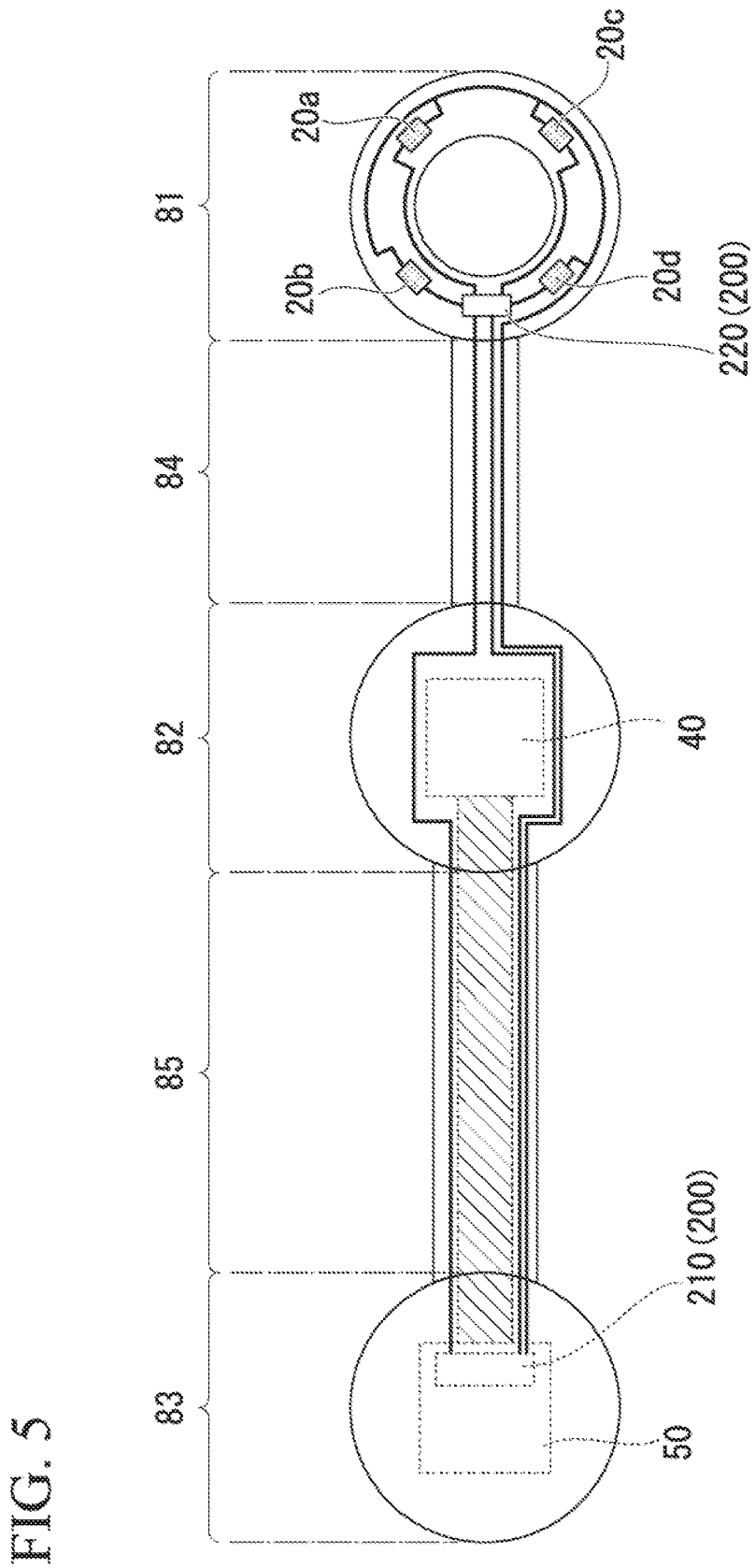
FIG. 5 is a view showing disposition and wiring of an illumination control circuit of the second configuration of the first embodiment.

Next, disposition of the components in the illumination control circuit 200 of the second configuration of the first embodiment and wirings in the flexible substrate 80 between the components provided in the illumination control circuit 200 will be described. FIG. 5 is a view showing disposition and wirings of the illumination control circuit 200 of the second configuration of the first embodiment. FIG. 5 shows the case in which the components of the illumination control circuit 200 are disposed on the flexible substrate 80 having the shape as shown in FIG. 1B.

As described above, the illumination control signal output unit 210 that configures the illumination control circuit 200 is disposed in the signal-processing unit 50 mounted on the signal-processing substrate section 83. The transistor array 220 that configures the illumination control circuit 200 is disposed together with the illumination unit 20 mounted on the illumination substrate section 81. Also, in the illumination control circuit 200, the current signal (the illumination control signal) of the current value Io connected between the illumination control signal output unit 210 and the transistor array 220, and the voltage signal of the power supply voltage VCC and the voltage signal of the ground are connected via the second wiring substrate section 85, the imaging element substrate section 82 and the first wiring substrate section 84. That is, as shown in FIG. 5, even in the illumination control circuit 200, like the illumination control circuit 100 of the first configuration, three wirings pass through the second wiring substrate section 85, the imaging element substrate section 82 and the first wiring substrate section 84.

According to the second configuration of the first embodiment, there is configured the capsule endoscope 1 in which an illumination control signal output unit (the illumination control signal output unit 210) includes a voltage-current conversion circuit (provided by the reference power supply 111, the operational amplifier 112, the resistor 113 and the transistor 214) configured to convert the reference voltage Vref into a current, and a first current mirror circuit (provided by the first input-side transistor 215 and the first output-side transistor 216) configured to output a signal of the current obtained by reproducing a value of the current converted by a voltage-current conversion circuit as an illumination control signal, and an illumination driving unit (the illumination driving unit 220) generates an illumination current obtained by reproducing a value of the current of the illumination control signal output from the first current mirror circuit by the transistors in a transistor array (the transistor array 220) and configures a second current mirror circuit corresponding to the white LEDs 20a to 20d (corresponding to the white LEDs 20a to 20d with the second input-side transistor 221 and the second output-side transistors 222a to 222d).

According to the above-mentioned configuration, operation and disposition, the illumination control circuit 200 controls light emission of the white LEDs 20a to 20d provided in the illumination unit 20 of the capsule endoscope 1. Here, in the illumination control circuit 200, the current value Io of the illumination current flowing to the white LEDs 20a to 20d is the same current value Io as the current value Io of the current generated by the voltage-current conversion circuit in the illumination control signal output unit 210. In the illumination control circuit 200, the white LEDs 20a to 20d can uniformly emit light without occurrence of a deviation in luminance (brightness) of the light emitted by the white LEDs 20a to 20d. Also, as the illumination control circuit 200 is used as the illumination control circuit configured to control light emission of the white LEDs 20a to 20d provided in the illumination unit 20 of the capsule endoscope 1, like the illumination control circuit 100 of the first configuration, performance (brightness) or quality (uniformity of illumination light) of the illumination unit 20 obtained by the capsule endoscope 1 can be easily secured.

In addition, even in the illumination control circuit 200, like the illumination control circuit 100 of the first configuration, light emission of the white LEDs 20a to 20d provided in the illumination unit 20 can be controlled by a smaller number of wirings (the number of signal lines) than in the related art. Light emission of the white LEDs 20a to 20d can be controlled and the illumination control circuit 200 can be easily applied to the capsule endoscope 1 without increasing the widths of the second wiring substrate section 85 and the first wiring substrate section 84 very much.

Further, even in the illumination control circuit 200, as described above, the first input-side transistor 215 and the first output-side transistor 216 that configure the first current mirror circuit in the illumination control signal output unit 210 have the same transistor size and matched properties, and the second input-side transistor 221 and the second output-side transistors 222a to 222d that configure the second current mirror circuit in the transistor array 220 have the same transistor size and matched properties. As the illumination control signal output unit 210 and the transistor array 220 in the illumination control circuit 200 are disposed at separated positions, even when an error occurs in the current value Io of the current output from the first current mirror circuit in the illumination control signal output unit 210 and the current value Io of the illumination current output from the second current mirror circuit in the transistor array 220, the current values Io of the illumination currents in the illumination unit 20 have the same current value, and like the illumination control circuit 100 of the first configuration, a deviation in luminance (brightness) of the light emitted by the white LEDs 20a to 20d does not occur.

Further, in the illumination control circuit 200, the case in which light emission of a larger number of white LEDs provided in the illumination unit 20 are controlled or a method of matching properties of the transistors provided in the first current mirror circuit and the second current mirror circuit can also be considered similar to the illumination control circuit 100 of the first configuration. Detailed description of the consideration method will be omitted.

Further, in the illumination control circuit 200, the case in which the first input-side transistor 215 and the first output-side transistor 216 that configure the first current mirror circuit, and the second input-side transistor 221 and the second output-side transistors 222a to 222d that configure the second current mirror circuit in the transistor array 220 have the same transistor size and matched properties has been described. However, in the current mirror circuit, when the properties of the transistors are matched, as the transistor size of the input-side transistor and the output-side transistor is varied, a ratio between the input current value and the output current value can be varied. In the illumination control circuit 200, properties of the current mirror circuit can be used.

<Third Configuration>

Figure 6:
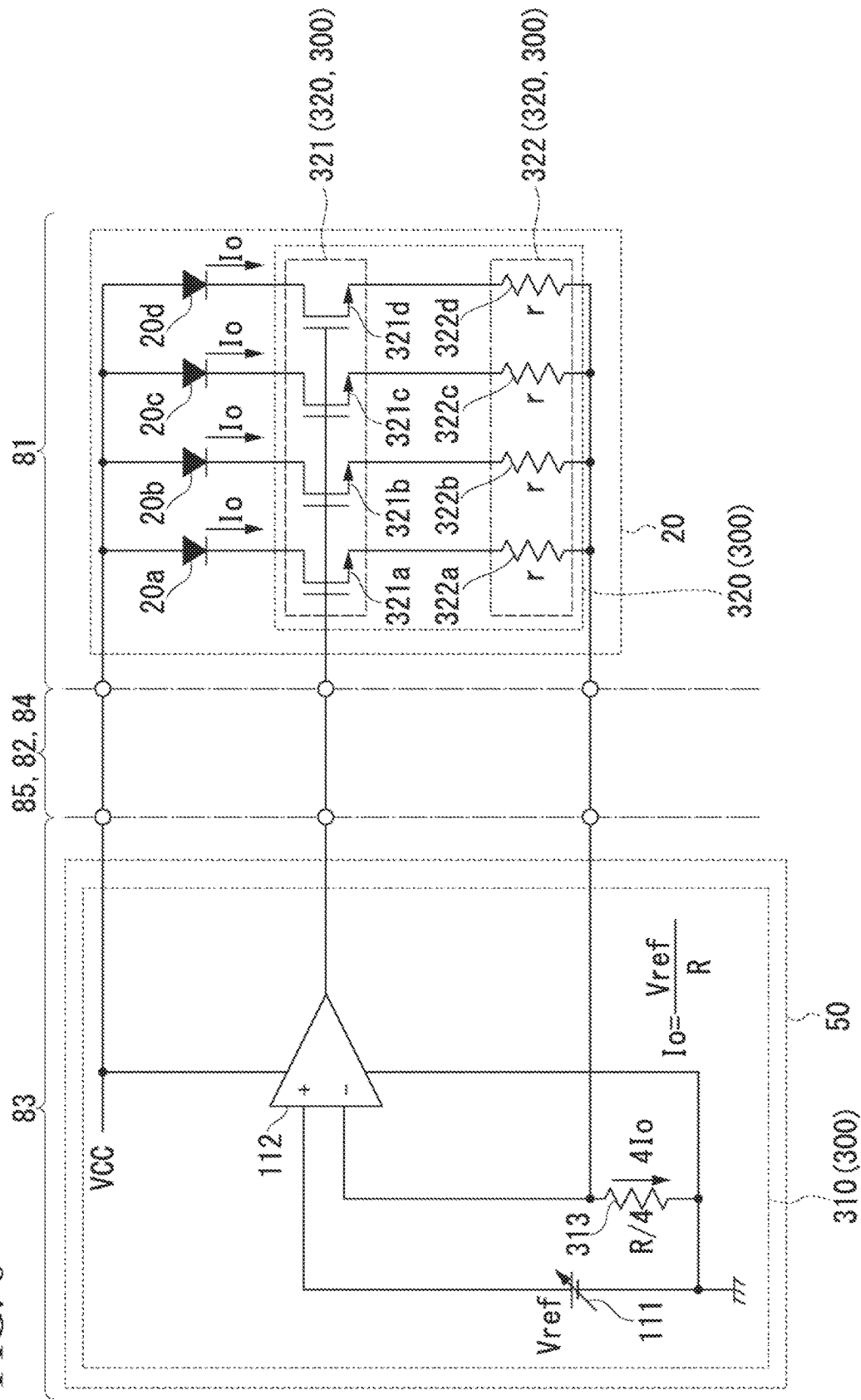
FIG. 6 is a circuit diagram showing a third configuration of the illumination control circuit of the first embodiment.

Next, a third configuration of the illumination control circuit of the first embodiment will be described. FIG. 6 is a circuit diagram showing the third configuration of the illumination control circuit of the first embodiment. An illumination control circuit 300 of the third configuration shown in FIG. 6 is provided by an illumination control signal output unit 310 and an illumination driving unit 320. In the illumination control circuit 300 of the third configuration, like the illumination control circuit 100 of the first configuration, the illumination control signal output unit 310 is disposed in the signal-processing unit 50 mounted on the signal-processing substrate section 83, and the illumination driving unit 320 is disposed together with the illumination unit 20 mounted on the illumination substrate section 81. Further, in the components of the illumination control circuit 300 of the third configuration, the same components as those of the illumination control circuit 100 of the first configuration are also included. Accordingly, even in the components of the illumination control circuit 300 of the third configuration, the same reference numerals designate the same components as those of the illumination control circuit 100 of the first configuration, and detailed description related to the components will be omitted.

Like the illumination control circuit 100 of the first configuration, the illumination control signal output unit 310 outputs the illumination control signal for controlling the driving of the white LEDs provided in the illumination unit 20 by the illumination driving unit 320, and controls the luminance (brightness) of the light emitted from the white LEDs. The illumination driving unit 320 directly drives the white LEDs provided in the illumination unit 20 according to the illumination control signal input from the illumination control signal output unit 310. In the illumination control circuit 300 of the third configuration, a transistor array 321 and a resistor array 322 are provided as the illumination driving unit 320. In the illumination control circuit 300 of the third configuration, the voltage-current conversion circuit, i.e., an amplifier circuit is provided by the components in the illumination control signal output unit 310 and the components in the illumination driving unit 320.

The illumination control signal output unit 310 is provided by a reference power supply 111, an operational amplifier 112 and a resistor 313. The reference power supply 111 and the operational amplifier 112 are the same components as those of the illumination control circuit 100 of the first configuration. However, in the illumination control signal output unit 310, a positive terminal of the reference power supply 111 is connected to the non-inverting input terminal of the operational amplifier 112, the inverting input terminal becomes a reference potential terminal of the illumination control signal output unit 310 to be connected to the one terminal of the resistor 313, and the output terminal becomes a voltage output terminal of the illumination control signal output unit 310. The reference voltage Vref is input into the non-inverting input terminal of the operational amplifier 112, and a voltage of the one terminal of the resistor 313 appears at the inverting input terminal. The resistor 313 is a resistor having a predetermined resistance value R/4. The resistor 313 has the one terminal that is connected to the inverting input terminal of the operational amplifier 112, i.e., the reference potential terminal, and the other terminal that is connected to the ground. Further, the voltage of the inverting input terminal serving as the reference potential terminal is the reference voltage Vref that appears by the virtual short of the operational amplifier 112.

The transistor array 321 is provided by a plurality of driving transistors disposed in an array and having the same transistor size and matched properties. FIG. 6 shows the transistor array 321 including four driving transistors 321a to 321d.

The resistor array 322 is provided by a plurality of resistors disposed in an array and having the same resistance value r and matched properties. FIG. 6 shows the resistor array 322 including four resistors 322a to 322d.

The illumination control signal output unit 310 is operated as a voltage-current conversion circuit, i.e., an amplifier by the configuration of the reference power supply 111, the operational amplifier 112, the resistor 313, the transistor array 321 and the resistor array 322.

In the illumination driving unit 320 shown in FIG. 6, the driving transistors 321a to 321d provided in the transistor array 321 and the corresponding resistors 322a to 322d provided in the resistor array 322 form sets and correspond to the four white LEDs 20a to 20d provided in the illumination unit 20. Then, the sets drive the corresponding white LEDs 20a to 20d, respectively.

More specifically, the set of the driving transistor 321a and the resistor 322a is operated as a part of the voltage-current conversion circuit, i.e., a part of the amplifier circuit, and drives the corresponding white LED 20a. In addition, the set of the driving transistor 321b and the resistor 322b is operated as a part of the voltage-current conversion circuit, i.e., a part of the amplifier circuit, and drives the corresponding white LED 20b. In addition, the set of the driving transistor 321c and the resistor 322c is operated as a part of the voltage-current conversion circuit, i.e., a part of the amplifier circuit, and drives the corresponding white LED 20c. In addition, the set of the driving transistor 321d and the resistor 322d is operated as a part of the voltage-current conversion circuit, i.e., a part of the amplifier circuit, and drives the corresponding white LED 20d.

The driving transistors 321a to 321d have gate terminals that are connected to the output terminal of the operational amplifier 112, source terminals that are connected to one terminal each of the resistors 322a to 322d, and drain terminals that are connected to cathode terminals of the corresponding white LEDs 20a to 20d. In addition, the other terminals of the resistors 322a to 322d are connected to the one terminal of the resistor 313 and the inverting input terminal (the reference potential terminal) of the operational amplifier 112. Further, anode terminals of the white LEDs 20a to 20d are connected to the power supply voltage VCC.

Next, an operation of the illumination control circuit 300 of the third configuration of the first embodiment will be described. As described above, in the illumination control circuit 300 of the third configuration of the first embodiment, the voltage-current conversion circuit part, i.e., the amplifier circuit, is provided by the components in the illumination control signal output unit 310 and the components in the illumination driving unit 320. A voltage between the signal lines to which the illumination control signal output unit 310 and the illumination driving unit 320 are connected is a voltage output to the inverting input terminal according to the reference voltage Vref input into the non-inverting input terminal of the operational amplifier 112 and a voltage according to a potential difference to the output terminal of the operational amplifier 112 (hereinafter, referred to as "a gate control voltage Vg"). That is, a voltage between the inverting input terminal serving as the reference potential terminal of the illumination control signal output unit 310 and the output terminal serving as the voltage output terminal of the illumination control signal output unit 310 is the gate control voltage Vg. In other words, a voltage signal of a gate control voltage Vg is output from the voltage output terminal of the illumination control signal output unit 310. In the illumination control circuit 300 of the third configuration, a voltage signal of the gate control voltage Vg output from the voltage output terminal of the illumination control signal output unit 310 (a potential difference between a potential of the voltage output terminal and a potential of the reference potential terminal) is the illumination control signal.

Here, the voltage signal of the gate control voltage Vg output from the voltage output terminal of the illumination control signal output unit 310 is input into the voltage input terminal of the transistor array 321 disposed on the illumination substrate section 81 and input into the gate terminals of the driving transistors 321a to 321d in the transistor array 321 via the second wiring substrate section 85, the imaging element substrate section 82 and the first wiring substrate section 84. Further, in the illumination control circuit 300, the power supply voltage VCC and the reference potential terminal of the illumination control signal output unit 310 are shared by the components in the illumination control circuit 300 (more specifically, the other terminals of the resistors 322a to 322d in the resistor array 322) and the illumination unit 20. Similar to the illumination control circuit 100 of the first configuration, the voltage signal of the power supply voltage VCC and the voltage signal of the reference potential terminal of the illumination control signal output unit 310 are also input into the illumination substrate section 81 via the second wiring substrate section 85, the imaging element substrate section 82 and the first wiring substrate section 84.

The driving transistors 321a to 321d generate the illumination currents of the current values Io flowing from the drain terminal to the source terminal according to the potential difference between the gate control voltage Vg input into the gate terminal and the voltage signal of the reference potential terminal of the illumination control signal output unit 310 via the corresponding resistors 322a to 322d connected to the source terminal, i.e., the voltage between the gate terminal and the source terminal.

Then, the illumination currents generated by the driving transistors 321a to 321d flow to the corresponding white LEDs 20a to 20d, respectively. More specifically, as shown in FIG. 6, the illumination current of the current value Io generated by the driving transistor 321a flows to the corresponding white LED 20a, the illumination current of the current value Io generated by the driving transistor 321b flows to the corresponding white LED 20b, the illumination current of the current value Io generated by the driving transistor 321c flows to the corresponding white LED 20c, and the illumination current of the current value Io generated by the driving transistor 321d flows to the corresponding white LED 20d.

Here, when the current value Io of the illumination current generated by each of the driving transistors 321a to 321d is the same current value as the illumination control circuit 100 of the first configuration, i.e., the current value Io=Vref/R (R is a resistance value of the resistor 113), a value of the resistor 313 may be R/4. That is, since the current having a value of 4Io flows to the resistor 313, it becomes Vref=4Io×R/4=RIo. Accordingly, it becomes Io=Vref/R.

Accordingly, the white LEDs 20a to 20d emit light with the luminance (brightness) according to the current value Io of the flowed illumination current.

Further, even in the illumination control circuit 300, like the illumination control circuit 100 of the first configuration, as the voltage value of the reference voltage Vref output by the reference power supply 111 is varied, the voltage value between the reference potential terminal and the voltage output terminal of the illumination control signal output unit 310 can be changed. That is, in the illumination control circuit 300, as the voltage value of the reference voltage Vref output by the reference power supply 111 is varied to change the voltage value of the gate control voltage Vg input into the gate terminals of the driving transistors 321a to 321d, the current value Io of the illumination current flowing to the white LEDs 20a to 20d can be controlled, and the luminance (brightness) of the light emitted from the white LEDs 20a to 20d can be controlled.

Figure 7:
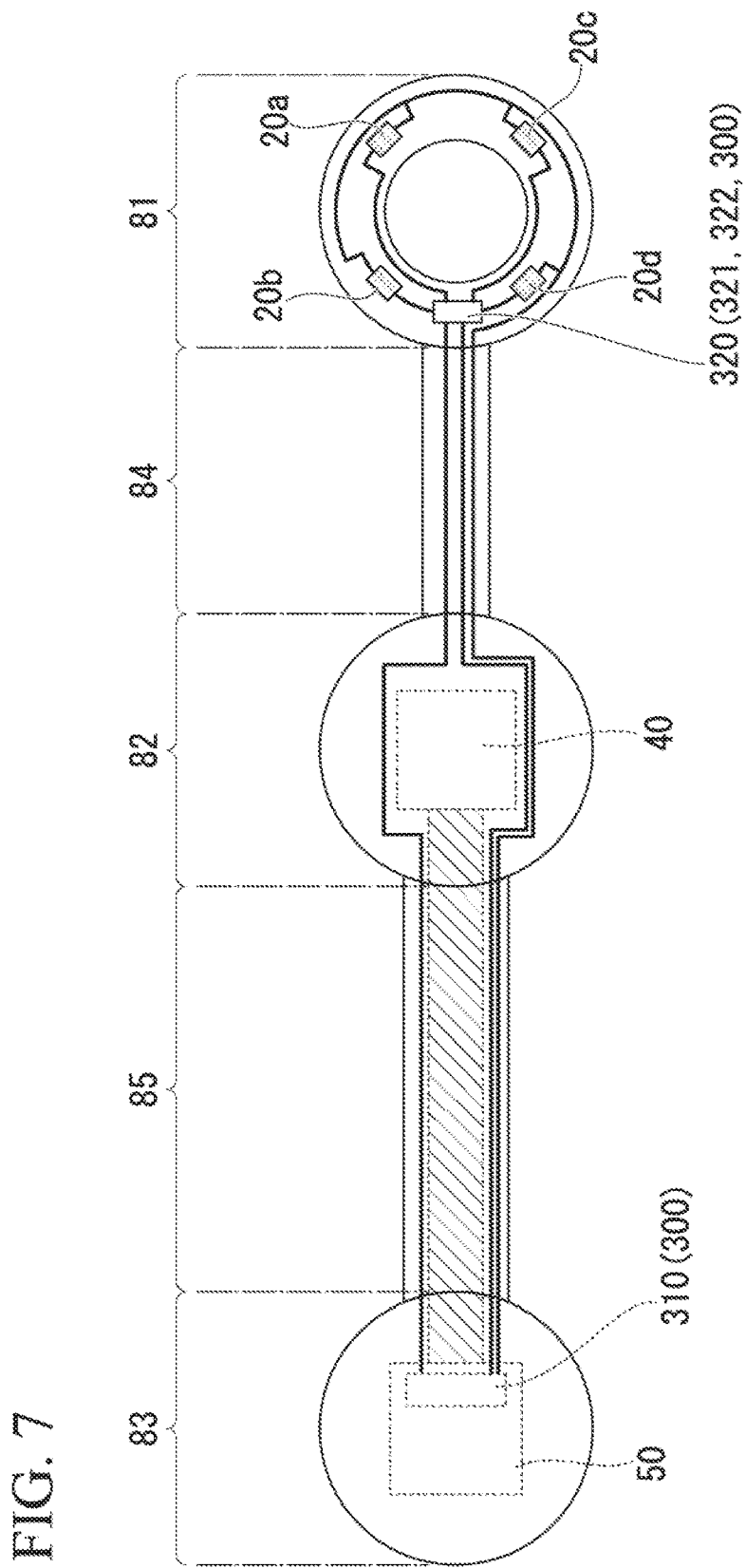
FIG. 7 is a view showing disposition and wiring of an illumination control circuit of the third configuration of the first embodiment.

Next, disposition of the components in the illumination control circuit 300 of the third configuration of the first embodiment and wirings in the flexible substrate 80 between the components provided in the illumination control circuit 300 will be described. FIG. 7 is a view showing the disposition and wirings of the illumination control circuit 300 of the third configuration of the first embodiment. FIG. 7 shows the case in which the components of the illumination control circuit 300 are disposed on the flexible substrate 80 having the shape shown in FIG. 1B.

As described above, the illumination control signal output unit 310 that configures the illumination control circuit 300 is disposed in the signal-processing unit 50 mounted on the signal-processing substrate section 83, and the illumination driving unit 320 is disposed together with the illumination unit 20 mounted on the illumination substrate section 81. Then, in the illumination control circuit 300, a voltage signal (an illumination control signal) of the gate control voltage Vg and the voltage signal of the reference potential terminal connected between the illumination control signal output unit 310 and the illumination driving unit 320, and the voltage signal of the power supply voltage VCC are connected via the second wiring substrate section 85, the imaging element substrate section 82 and the first wiring substrate section 84. That is, as shown in FIG. 7, even in the illumination control circuit 300, like the illumination control circuit 100 of the first configuration and the illumination control circuit 200 of the second configuration, three wirings pass through the second wiring substrate section 85, the imaging element substrate section 82 and the first wiring substrate section 84.

According to the third configuration of the first embodiment, there is configured the capsule endoscope 1 in which an illumination control signal output unit (the illumination control signal output unit 310) includes an amplifier circuit (a voltage-current conversion circuit: provided by the illumination control signal output unit 310 and the illumination driving unit 320) configured to output a signal of a voltage according to the reference voltage Vref as an illumination control signal, an illumination driving unit (the illumination driving unit 320) further includes a resistor array (the resistor array 322) including a plurality of resistors (the resistors 322a to 322d) corresponding to transistors in a transistor array (the transistor array 321) and connected to a reference potential of the amplifier circuit, the transistors in the transistor array 321 are configured as the driving transistors (the driving transistors 321a to 321d) configured to drive the corresponding white LEDs 20a to 20d, and the driving transistors 321a to 321d generate the illumination current according to the potential difference between the potential of the illumination control signal input into the gate terminal and the reference potential connected via the corresponding resistors 322a to 322d in the resistor array 322.

According to the above-mentioned configuration, operation and disposition, the illumination control circuit 300 controls emission of light of the white LEDs 20a to 20d provided in the illumination unit 20 of the capsule endoscope 1. Here, in the illumination control circuit 300, the current value Io of the illumination current flowing to the white LEDs 20a to 20d is the same current value Io generated by the driving transistors 321a to 321d in the transistor array 321 provided in the illumination driving unit 320. In the illumination control circuit 300, the light can be uniformly emitted without occurrence of a deviation in luminance (brightness) of the light emitted by the white LEDs 20a to 20d. Then, as the illumination control circuit 300 is used as the illumination control circuit configured to control light emission of the white LEDs 20a to 20d provided in the illumination unit 20 of the capsule endoscope 1, like the illumination control circuit 100 of the first configuration and the illumination control circuit 200 of the second configuration, performance (brightness) or quality (uniformity of illumination light) of the illumination unit 20 obtained by the capsule endoscope 1 can be easily secured.

In addition, even in the illumination control circuit 300, like the illumination control circuit 100 of the first configuration and the illumination control circuit 200 of the second configuration, light emission of the white LEDs 20a to 20d provided in the illumination unit 20 is controlled by a smaller number of wirings (the number of signal lines) than in the related art. Light emission of the white LEDs 20a to 20d can be controlled and the illumination control circuit 300 can be easily applied to the capsule endoscope 1 without increasing the widths of the second wiring substrate section 85 and the first wiring substrate section 84 very much.

Further, in the illumination control circuit 300, as described above, the driving transistors 321a to 321d in the transistor array 321 provided in the illumination driving unit 320 have the same transistor size and matched properties. In addition, the resistors 322a to 322d in the resistor array 322 provided in the illumination driving unit 320 have the same resistance value r and matched properties. That is, the components in the illumination driving unit 320 are matched with each other regardless of the illumination control signal output unit 310 disposed at a position separated in the illumination control circuit 300. In the illumination control circuit 300, a deviation also does not occur in the luminance (brightness) of the light emitted by the white LEDs 20a to 20d without the influence of the illumination control signal output unit 310.

Further, in the illumination control circuit 300, the case in which light emission of a larger number of white LEDs provided in the illumination unit 20 is controlled or a method of matching properties of the driving transistor in the transistor array 321 provided in the illumination driving unit 320 and the resistor of the resistor array 322 provided in the illumination driving unit 320 can be considered similarly to the illumination control circuit 100 of the first configuration. Detailed description related to the consideration method will be omitted.

As described above, in the first embodiment, in the capsule endoscope 1, the illumination control circuit configured to control light emission of the white LEDs provided in the illumination unit 20 is disposed to be divided onto the signal-processing substrate section 83 and the illumination substrate section 81 of the flexible substrate 80 integrally formed in a shape in which the substrate sections are arranged in an row in sequence of the illumination substrate section 81, the first wiring substrate section 84, the imaging element substrate section 82, the second wiring substrate section 85 and the signal-processing substrate section 83. Here, the illumination driving unit configured to directly drive the plurality of white LEDs is disposed on the illumination substrate section 81, and the illumination control signal output unit configured to control the illumination driving unit to control the driving of the white LEDs is disposed on the signal-processing substrate section 83. Accordingly, in the first embodiment, the plurality of wirings of the white LEDs connected between the illumination driving unit and the white LEDs to drive the white LEDs do not pass through the regions of the second wiring substrate section 85, the imaging element substrate section 82 and the first wiring substrate section 84, and only a small number of wirings configured to control the driving of the white LEDs by the illumination driving unit pass therethrough. Accordingly, in the first embodiment, the wirings having a sufficient size required to secure the performance (brightness) of illumination or the quality (uniformity of illumination light) obtained by the capsule endoscope 1 can be formed in the flexible substrate 80 while maintaining the accommodation of the capsule endoscope 1 in the capsule housing 10 without increasing the widths of the second wiring substrate section 85 and the first wiring substrate section 84 very much.

Further, in the first embodiment, while the case in which the illumination driving unit configured to directly drive the plurality of white LEDs is disposed on the illumination substrate section 81 has been described, the substrate on which the illumination driving unit is disposed is not limited to the illumination substrate section 81, but the illumination driving unit may be disposed on another substrate.

<Second Embodiment>

Next, in the capsule endoscope 1 of the embodiment, another illumination control circuit configured to control light emission of white LEDs provided in the illumination unit 20 will be described.

<First Configuration>

Figure 8:
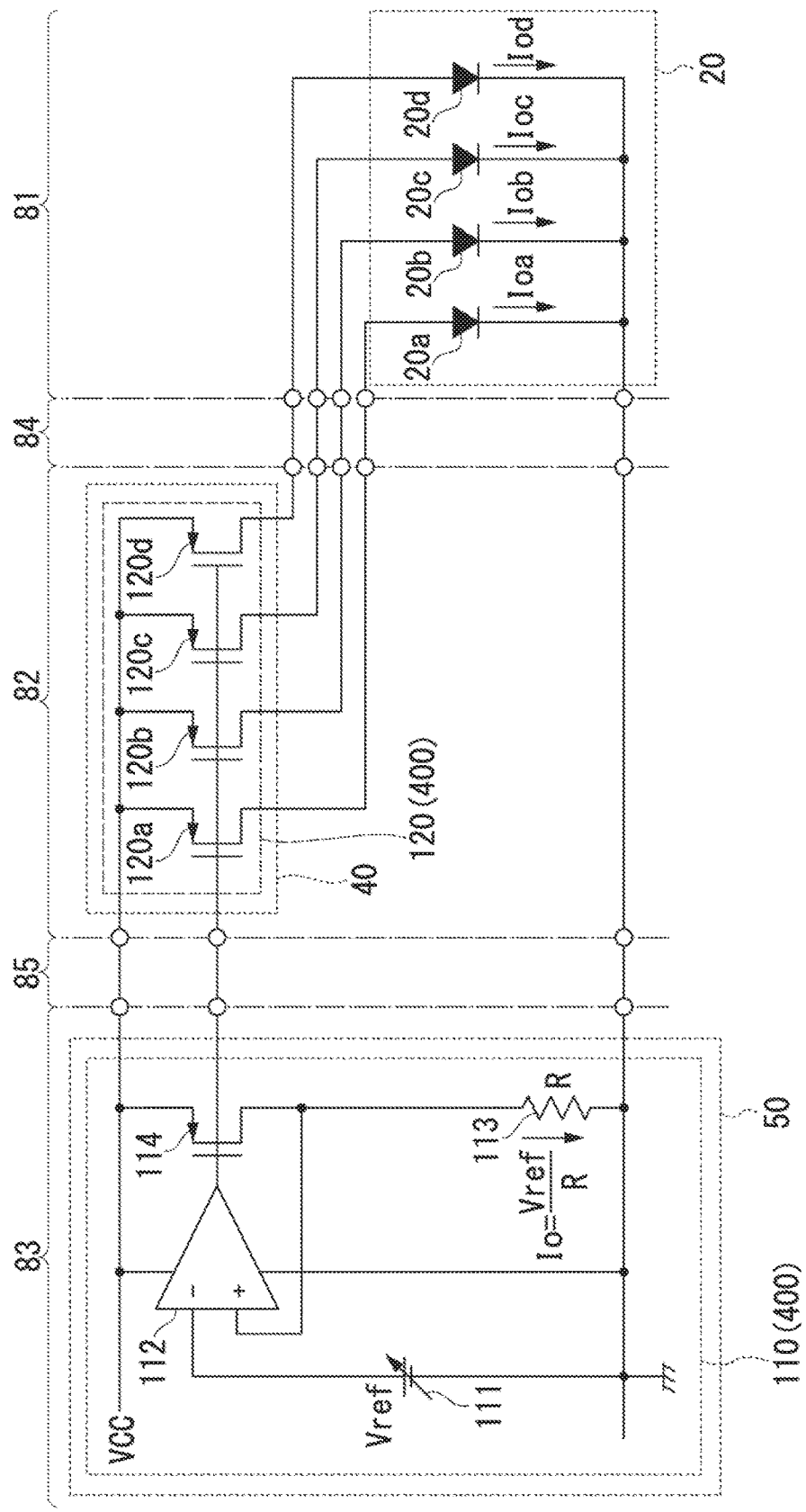
FIG. 8 is a circuit diagram showing a first configuration of an illumination control circuit of a second embodiment of the present invention.

First, a first configuration of the illumination control circuit of the second embodiment will be described. FIG. 8 is a circuit diagram showing the first configuration of the illumination control circuit of the second embodiment. An illumination control circuit 400 of the first configuration shown in FIG. 8 is provided by the illumination control signal output unit 110 and the illumination driving unit 120. In the illumination control circuit 400 of the first configuration, the illumination control signal output unit 110 is disposed in the signal-processing unit 50 mounted on the signal-processing substrate section 83, and the illumination driving unit 120 is disposed in the imaging element 40 mounted on the imaging element substrate section 82. A configuration of the illumination control circuit 400 of the first configuration is the same as that of the illumination control circuit 100 of the first configuration of the first embodiment except that the illumination driving unit 120 is disposed at a different position. An operation of the illumination control circuit 400 of the first configuration is also the same as that of the illumination control circuit 100 of the first configuration of the first embodiment. Accordingly, detailed description related to the configuration and operation of the illumination control circuit 400 of the first configuration will be omitted.

Figure 9:
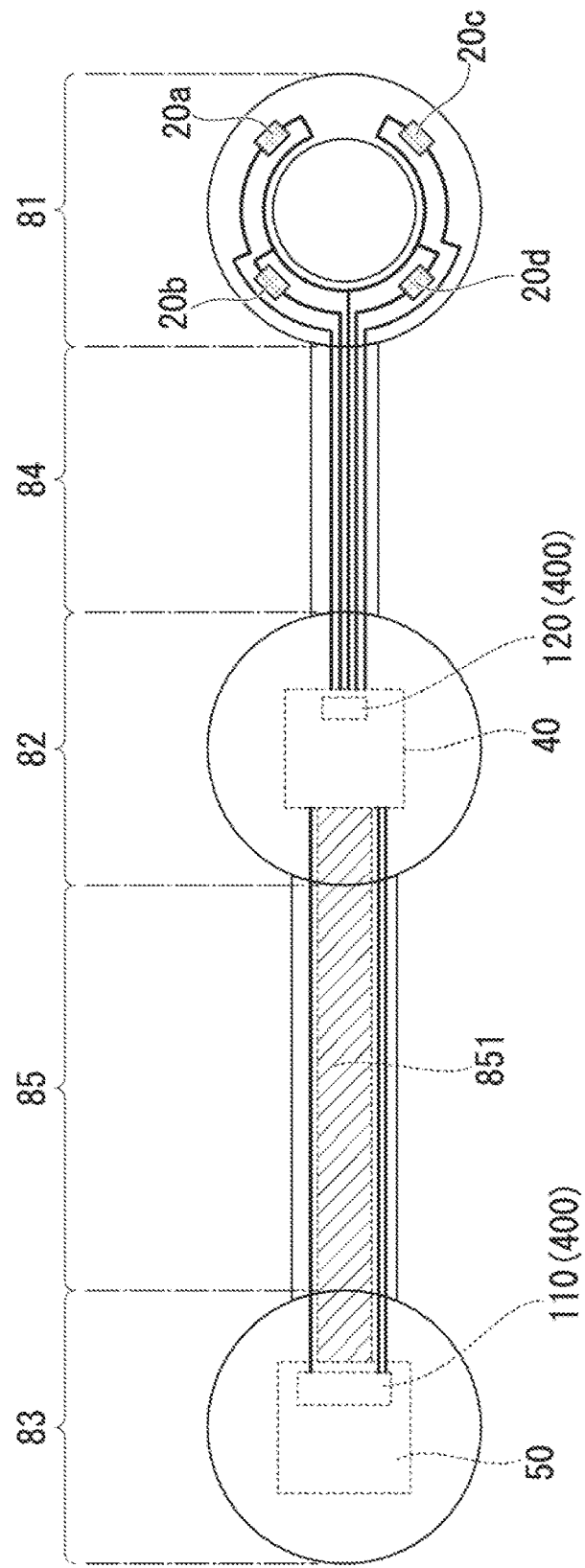
FIG. 9 is a view showing disposition and wiring of the illumination control circuit of the first configuration of the second embodiment.

Next, disposition of the components in the illumination control circuit 400 of the first configuration of the second embodiment and wirings in the flexible substrate 80 between the components provided in the illumination control circuit 400 will be described. FIG. 9 is a view showing the disposition and the wirings of the illumination control circuit 400 of the first configuration of the second embodiment. FIG. 9 shows the case in which the components of the illumination control circuit 400 are disposed on the flexible substrate 80 having the shape shown in FIG. 1B.

As described above, the illumination control signal output unit 110 that configures the illumination control circuit 400 is disposed in the signal-processing unit 50 mounted on the signal-processing substrate section 83, and the illumination driving unit 120 (the transistor array 120) is disposed in the imaging element 40 mounted on the imaging element substrate section 82. In the illumination control circuit 400, a voltage signal (an illumination control signal) of the gate control voltage VGS connected between the illumination control signal output unit 110 and the transistor array 120, and a voltage signal of the power supply voltage VCC and a voltage signal of the ground are connected to the imaging element 40 via the second wiring substrate section 85. Then, in the illumination control circuit 400, a plurality of current signals of the illumination current of the current value Io connected between the transistor array 120 and the white LEDs 20a to 20d provided in the illumination unit 20 are connected via the first wiring substrate section 84. That is, as shown in FIG. 9, in the illumination control circuit 400, three wirings pass through the second wiring substrate section 85, and five wirings pass through the first wiring substrate section 84.

According to the first configuration of the second embodiment, there is configured the capsule endoscope 1 in which an illumination driving unit (the illumination driving unit 120) is formed as a component provided in the imaging element 40 mounted on the imaging element substrate section 82 when disposed on the imaging element substrate section 82.

According to the above-mentioned disposition, even when the illumination control circuit 400 is used as the illumination control circuit configured to control light emission of the white LEDs 20a to 20d provided in the illumination unit 20 of the capsule endoscope 1, like the case in which the illumination control circuit 100 of the first configuration of the first embodiment is used as the illumination control circuit, the illumination control circuit 400 can be easily applied to the capsule endoscope 1 without increasing the widths of the second wiring substrate section 85 and the first wiring substrate section 84 very much. Then, like the case in which the illumination control circuit 100 of the first configuration of the first embodiment is used as the illumination control circuit, the capsule endoscope 1 that uses the illumination control circuit 400 as the illumination control circuit can easily secure the performance (brightness) or quality (uniformity of illumination light) of the obtained illumination unit 20.

Further, as shown in FIGS. 8 and 9, in the illumination control circuit 400, the number of wirings (the number of signal lines) formed at the first wiring substrate section 84 is larger than that of the illumination control circuit 100 of the first configuration of the first embodiment. However, originally, since the number of wirings smaller than that of a wiring group 851 of signals transmitted and received between the imaging element 40 and the signal-processing unit 50 are formed at the first wiring substrate section 84, an effect of an increase in the number of wirings of the first wiring substrate section 84 does not occur. Instead of this, as the transistor array 120 is not disposed on the illumination substrate section 81, it is effective because a region in which the plurality of white LEDs can be mounted on the illumination substrate section 81 is increased.

In addition, in the illumination control circuit 400, the transistor array 120 is disposed in the imaging element 40. In the capsule endoscope 1 that uses the illumination control circuit 400 as the illumination control circuit, the driving transistors provided in the transistor array 120 are not provided by individual transistors from the relation in which the plurality of white LED are mounted on the illumination substrate section 81, and properties of the driving transistors can be easily matched in the imaging element 40.

<Second Configuration>

Figure 10:
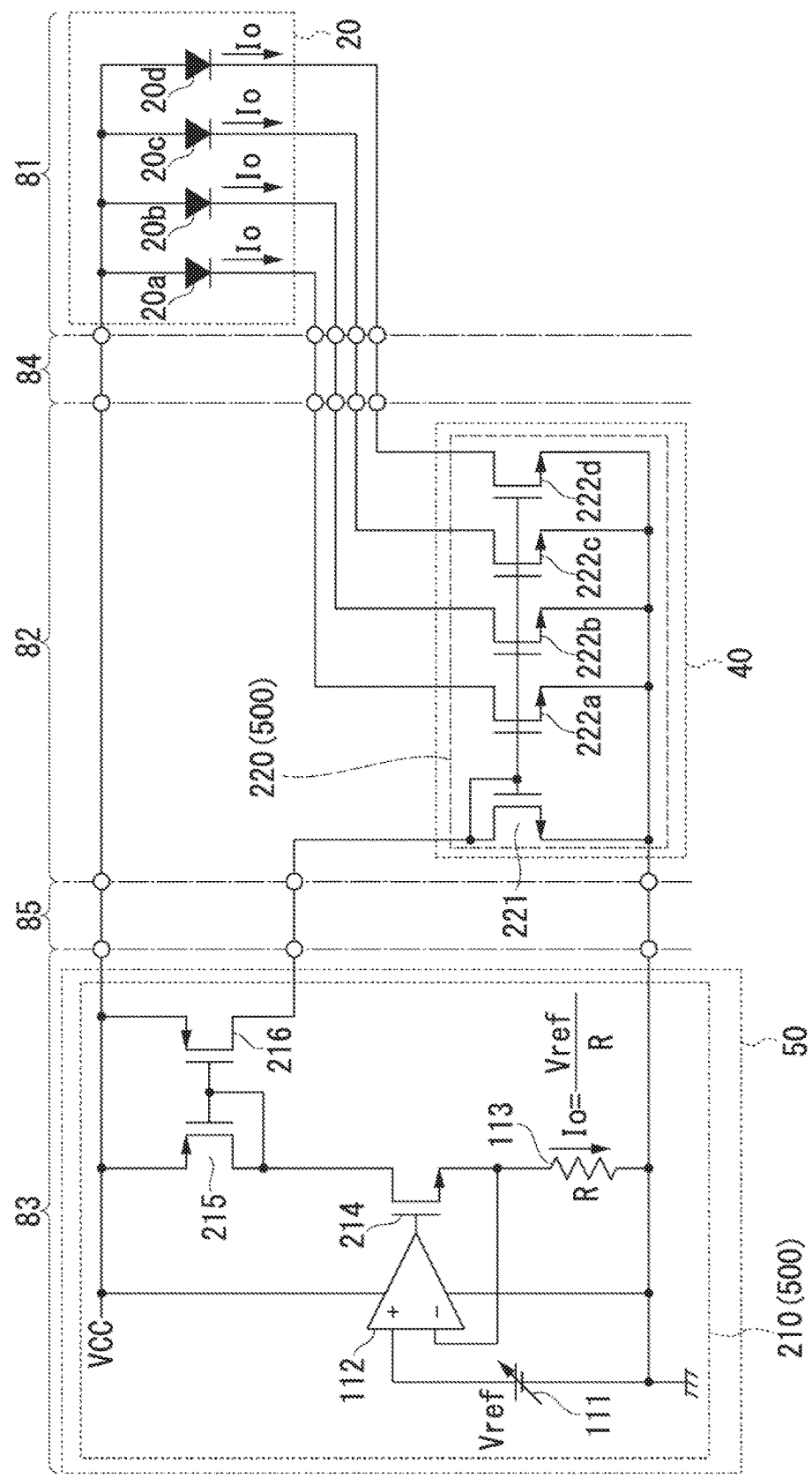
FIG. 10 is a circuit diagram showing a second configuration of the illumination control circuit of the second embodiment.

Next, a second configuration of the illumination control circuit of the second embodiment will be described. FIG. 10 is a circuit diagram showing the second configuration of the illumination control circuit of the second embodiment. An illumination control circuit 500 of the second configuration shown in FIG. 10 is provided by the illumination control signal output unit 210 and the illumination driving unit 220. In the illumination control circuit 500 of the second configuration, like the illumination control circuit 400 of the first configuration, the illumination control signal output unit 210 is disposed in the signal-processing unit 50 mounted on the signal-processing substrate section 83, and the illumination driving unit 220 is disposed in the imaging element 40 mounted on the imaging element substrate section 82. A configuration of the illumination control circuit 500 of the second configuration is the same as that of the illumination control circuit 200 of the second configuration of the first embodiment except that the illumination driving unit 220 is disposed at a different position. An operation of the illumination control circuit 500 of the second configuration is also the same as that of the illumination control circuit 200 of the second configuration of the first embodiment. Accordingly, detailed description related to the configuration and the operation of the illumination control circuit 500 of the second configuration will be omitted.

Figure 11:
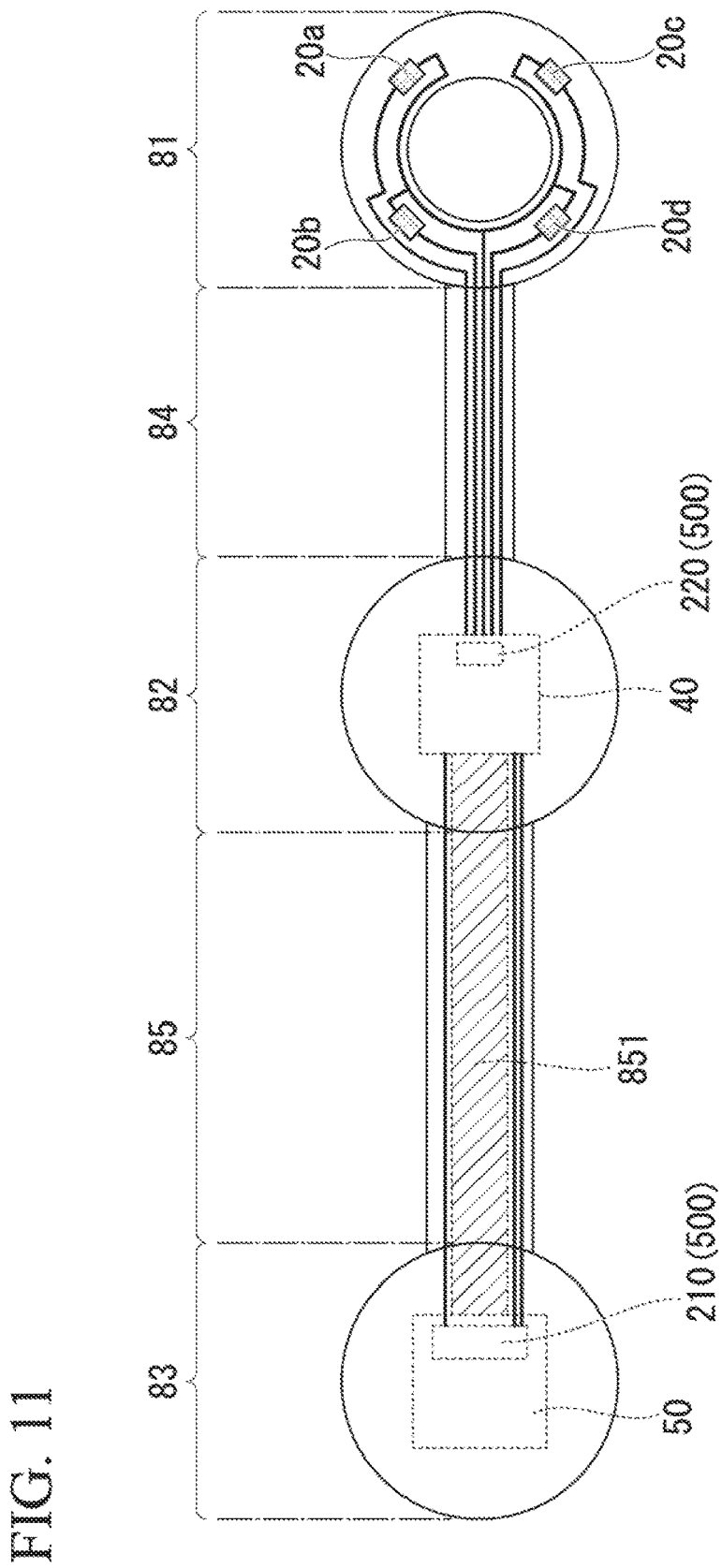
FIG. 11 is a view showing disposition and wiring of the illumination control circuit of the second configuration of the second embodiment.

Next, disposition of the components in the illumination control circuit 500 of the second configuration of the second embodiment and wirings in the flexible substrate 80 between the components provided in the illumination control circuit 500 will be described. FIG. 11 is a view showing the disposition and the wirings of the illumination control circuit 500 of the second configuration of the second embodiment. FIG. 11 shows the case in which the components of the illumination control circuit 500 are disposed on the flexible substrate 80 having the shape shown in FIG. 1B.

As described above, the illumination control signal output unit 210 that configures the illumination control circuit 500 is disposed in the signal-processing unit 50 mounted on the signal-processing substrate section 83, and the illumination driving unit 220 (the transistor array 220) is disposed in the imaging element 40 mounted on the imaging element substrate section 82. In the illumination control circuit 500, the current signal (the illumination control signal) of the current value Io connected between the illumination control signal output unit 110 and the transistor array 120, and the voltage signal of the power supply voltage VCC and the voltage signal of the ground are connected to the imaging element 40 via the second wiring substrate section 85. Then, in the illumination control circuit 500, a plurality of current signals of the illumination current of the current value Io connected between the transistor array 220 and the white LEDs 20*a* to 20*d* provided in the illumination unit 20 are connected via the first wiring substrate section 84. That is, as shown in FIG. 11, even in the illumination control circuit 500, like the illumination control circuit 400 of the first configuration, three wirings pass through the second wiring substrate section 85, and five wirings pass through the first wiring substrate section 84.

According to the above-mentioned disposition, even when the illumination control circuit 500 is used as the illumination control circuit configured to control light emission of the white LEDs 20*a* to 20*d* provided in the illumination unit 20 of the capsule endoscope 1, like the case in which the illumination control circuit 200 of the second configuration of the first embodiment is used as the illumination control circuit, the illumination control circuit 500 can be easily applied to the capsule endoscope 1 without increasing the widths of the second wiring substrate section 85 and the first wiring substrate section 84 very much. Then, like the case in which the illumination control circuit 200 of the second configuration of the first embodiment is used as the illumination control circuit, the capsule endoscope 1 that uses the illumination control circuit 500 as the illumination control circuit can easily secure performance (brightness) or quality (uniformity of illumination light) of the obtained illumination unit 20.

Further, as shown in FIGS. 10 and 11, even in the illumination control circuit 500, the number of wirings (the number of signal lines) formed at the first wiring substrate section 84 is larger than that of the illumination control circuit 200 of the second configuration of the first embodiment. However, like the illumination control circuit 400 of the first configuration of the second embodiment, as the transistor array 220 is not disposed on the illumination substrate section 81, it is effective because a region in which the plurality of white LEDs can be mounted on the illumination substrate section 81 is increased, or properties of the driving transistors provided in the transistor array 120 are easily matched in the imaging element 40.

<Third Configuration>

Figure 12:
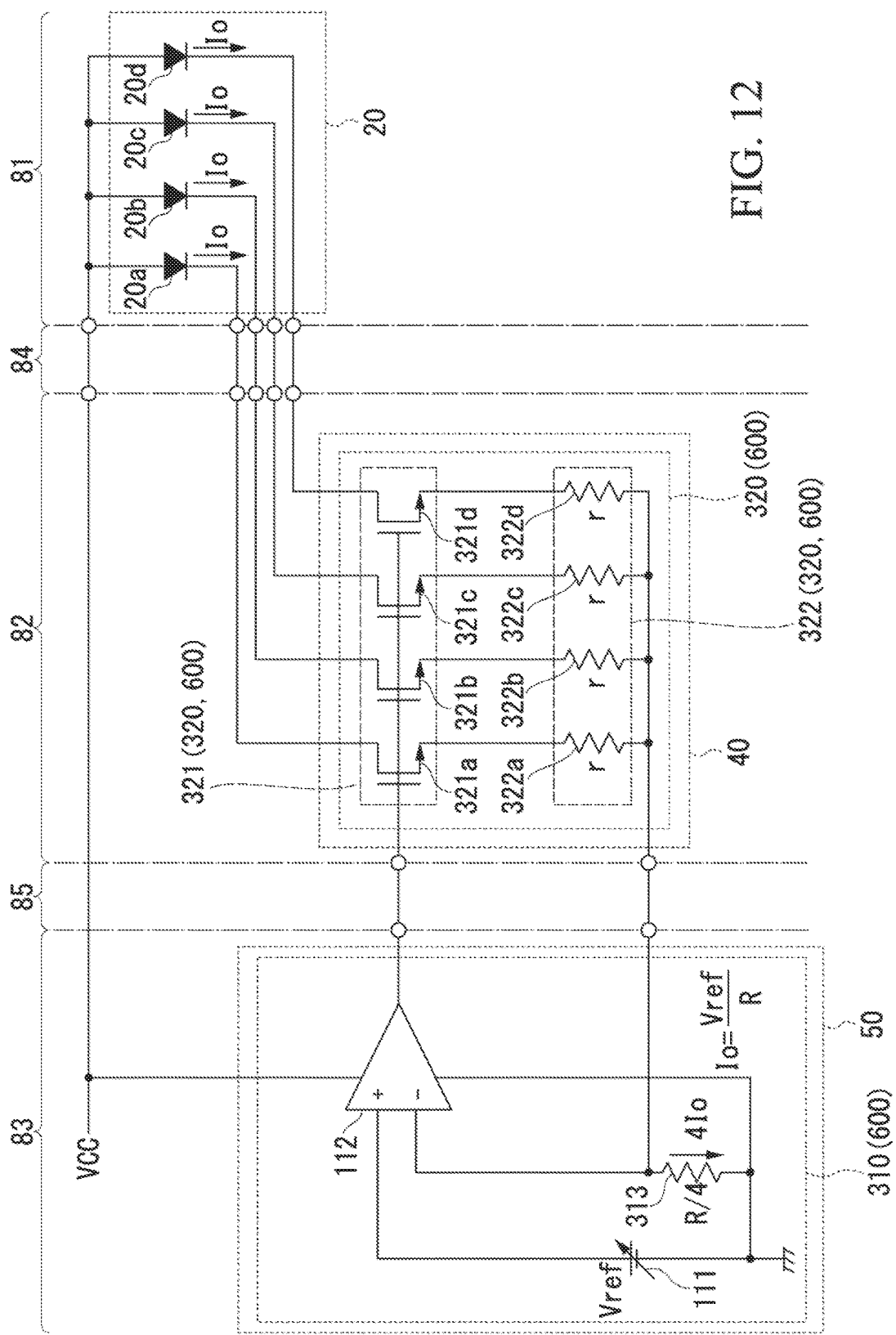
FIG. 12 is a circuit diagram showing a third configuration of the illumination control circuit of the second embodiment.

Next, a third configuration of the illumination control circuit of the second embodiment will be described. FIG. 12 is a circuit diagram showing the third configuration of the illumination control circuit of the second embodiment. An illumination control circuit 600 of the third configuration shown in FIG. 12 is provided by the illumination control signal output unit 310 and the illumination driving unit 320. In the illumination control circuit 600 of the third configuration, like the illumination control circuit 400 of the first configuration, the illumination control signal output unit 310 is disposed in the signal-processing unit 50 mounted on the signal-processing substrate section 83, and the illumination driving unit 320 is disposed in the imaging element 40 mounted on the imaging element substrate section 82. A configuration of the illumination control circuit 600 of the third configuration is the same as that of the illumination control circuit 300 of the third configuration of the first embodiment except that the illumination driving unit 320 is disposed at a different position. An operation of the illumination control circuit 600 of the third configuration is the same as that of the illumination control circuit 300 of the third configuration of the first embodiment. Accordingly, detailed description of the configuration and the operation of the illumination control circuit 600 of the third configuration will be omitted.

Next, disposition of the components in the illumination control circuit 600 of the third configuration of the second embodiment and wirings in the flexible substrate 80 between the components provided in the illumination control circuit 600 will be described. FIG. 13 is a view showing the disposition and the wirings of the illumination control circuit 600 of the third configuration of the second embodiment. FIG. 1B shows the case in which the components of the illumination control circuit 600 are disposed on the flexible substrate 80 having the shape shown in FIG. 1B.

As described above, the illumination control signal output unit 310 that configures the illumination control circuit 600 is disposed in the signal-processing unit 50 mounted on the signal-processing substrate section 83, and the illumination driving unit 320 (the transistor array 321 and the resistor array 322) is disposed in the imaging element 40 mounted on the imaging element substrate section 82. In the illumination control circuit 600, the voltage signal of the reference potential terminal connected between the voltage signal (the illumination control signal) of the gate control voltage Vg connected between the illumination control signal output unit 310 and the transistor array 321 provided in the illumination driving unit 320 and the resistor array 322 provided in the illumination driving unit 320, and the voltage signal of the power supply voltage VCC are connected to the imaging element 40 via the second wiring substrate section 85. Then, in the illumination control circuit 600, the plurality of current signals of the illumination current of the current value Io connected between the transistor array 321 and the white LEDs 20*a* to 20*d* provided in the illumination unit 20 are connected via the first wiring substrate section 84. That is, as shown in FIG. 13, even in the illumination control circuit 600, like the illumination control circuit 400 of the first configuration, three wirings pass through the second wiring substrate section 85, and five wirings pass through the first wiring substrate section 84.

According to the above-mentioned disposition, even when the illumination control circuit 600 is used as the illumination control circuit configured to control light emission of the white LEDs 20*a* to 20*d* provided in the illumination unit 20 of the capsule endoscope 1, like the case in which the illumination control circuit 300 of the third configuration of the first embodiment is used as the illumination control circuit, the illumination control circuit 600 can be easily applied to the capsule endoscope 1 without increasing the widths of the second wiring substrate section 85 and the first wiring substrate section 84 very much. Then, like the case in which the illumination control circuit 300 of the third configuration of the first embodiment is used as the illumination control circuit, the capsule endoscope 1 that uses the illumination control circuit 600 as the illumination control circuit, performance (brightness) or quality (uniformity of illumination light) of the obtained illumination unit 20 can be easily secured.

Further, as shown in FIGS. 12 and 13, even in the illumination control circuit 600, the number of wirings (the number of signal lines) formed at the first wiring substrate section 84 is larger than that of the illumination control circuit 300 of the third configuration of the first embodiment. However, like the illumination control circuit 400 of the first configuration of the second embodiment, as the illumination driving unit 320 (the transistor array 321 and the resistor array 322) is not disposed on the illumination substrate section 81, it is effective because a region in which the plurality of white LEDs can be mounted on the illumination substrate section 81 is increased, or matching of properties of the driving transistors provided in the transistor array 321 or matching of properties of the resistance values or the like of the resistors provided in the resistor array 322 can be easily performed in the imaging element 40.

As described above, in the second embodiment, in the capsule endoscope 1, the illumination control circuit configured to control light emission of the white LEDs provided in the illumination unit 20 is disposed to be divided onto the signal-processing substrate section 83 and the imaging element substrate section 82 of the flexible substrate 80 integrally formed in a shape in which the substrate sections are arranged in a row in sequence of the illumination substrate section 81, the first wiring substrate section 84, the imaging element substrate section 82, the second wiring substrate section 85 and the signal-processing substrate section 83. Here, the illumination driving unit configured to directly drive the plurality of white LEDs is disposed on the imaging element substrate section 82, and the illumination control signal output unit configured to control the illumination driving unit for controlling the driving of the white LEDs is disposed on the signal-processing substrate section 83. Accordingly, in the second embodiment, while the number of the plurality of wirings of each of the white LEDs connected between the illumination driving unit and the white LEDs to drive the white LEDs is equal to that of the related art, only a number of wirings smaller than that of the illumination control signals for controlling the illumination driving unit by the illumination control signal output unit pass through the region of the second wiring substrate section 85. Accordingly, in the second embodiment, the accommodation of the capsule endoscope 1 into the capsule housing 10 can be maintained while the wirings having a sufficient size required for securing performance (brightness) or quality (uniformity of illumination light) of the obtained illumination are formed in the first wiring substrate section 84 without increasing the width of the second wiring substrate section 85 very much.

As described above, according to the aspect for performing the present invention, in the capsule endoscope, the illumination control circuit configured to control light emission of the plurality of light-emitting elements provided in the illumination unit is disposed to be divided onto the signal-processing substrate section, the imaging element substrate section or the illumination substrate section of the flexible substrate integrally formed in a shape in which the substrate sections are arranged in a row in sequence of the illumination substrate section, the first wiring substrate section, the imaging element substrate section, the second wiring substrate section and the signal-processing substrate section 83. Here, the components in the illumination control circuit connected to the plurality of light-emitting elements provided in the illumination unit are disposed on the imaging element substrate section or the illumination substrate section. Accordingly, there is no need to form the plurality of wirings of the signals connected to the plurality of light-emitting elements provided in the illumination unit at the second wiring substrate section between the signal-processing substrate section and the imaging element substrate section, and the number of wirings related to light emission control of the light-emitting elements provided in the illumination unit formed on the second wiring substrate section can be reduced. Accordingly, in the capsule endoscope, the wirings having a sufficient size to secure performance (brightness) or quality (uniformity of illumination light) of illumination obtained by the capsule endoscope can be formed in the flexible substrate while holding accommodation of the flexible substrate on which the components are mounted into the capsule housing.

Further, the case in which the illumination driving unit is disposed on the illumination substrate section in the first embodiment and the illumination driving unit is disposed on the imaging element substrate section in the second embodiment has been described. That is, in either of the first embodiment and the second embodiment, the case in which the illumination control signal output unit is disposed on the signal-processing substrate section has been described. However, the substrate at which the signal-processing substrate section is disposed is not limited to the signal-processing substrate section. That is, like the illumination driving unit, the signal-processing substrate section may also be disposed at the imaging element substrate section. In this case, there is no need to form the wirings of the illumination control signal or the like to control the illumination driving unit by the illumination control signal output unit at the second wiring substrate section. In addition, matching of the properties of the components of the illumination control circuit can be easily performed in the imaging element 40.

Further, the configuration in which, in the first embodiment and the second embodiment, the illumination control signal output unit that configures the illumination control circuit is disposed in the signal-processing unit 50, i.e., built in the signal-processing unit 50 and, in the second embodiment, the illumination driving unit that configures the illumination control circuit is disposed in the imaging element 40, i.e., built in the imaging element 40 has been described. That is, the configuration formed on the same silicon substrate (a so-called IC chip) has been described. However, when the illumination control signal output unit and the illumination driving unit that configure the illumination control circuit are disposed on the signal-processing substrate section 83 or the imaging element substrate section 82, the components are not limited to the configuration being built in the corresponding components of the capsule endoscope. That is, the illumination control signal output unit and the illumination driving unit that configure the illumination control circuit may be separately manufactured, at each independent single IC chip, from the signal-processing unit 50 and the imaging element 40. Even in this case, the illumination control signal output unit and the illumination driving unit that are singly manufactured are disposed in the substrate on which the components of the capsule endoscope are mounted.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A capsule endoscope comprising:
a flexible substrate which is integrally formed by disposing an illumination substrate section, a first wiring substrate section, an imaging element substrate section, a second wiring substrate section, and a signal-processing substrate section in a row in sequence, the flexible substrate being accommodated in a capsule housing, wherein the imaging element substrate section is provided with an imaging element mounted on the imaging element substrate section and provided to output a pixel signal of a photographed subject, the imaging element including a plurality of pixels disposed in a two-dimensional matrix, wherein the signal-processing substrate section is provided with a signal-processing circuit mounted on the signal-processing substrate section, the signal-processing circuit being provided to control photographing of the subject in the imaging element and generate an image by performing predetermined types of image processing to the pixel signal output from the imaging element, wherein the illumination substrate section is provided with a plurality of light-emitting elements mounted on the illumination substrate, the plurality of light-emitting elements being included in an illumination unit provided to radiate light onto the photographed subject, wherein the first wiring substrate section is provided such that wirings for signals passing between the illumination substrate section and the imaging element substrate section are formed, and wherein the second wiring substrate section is provided such that wirings for signals passing between the imaging element substrate section and the signal-processing substrate section are formed, and an illumination control circuit which includes:

an illumination control signal output circuit provided to output an illumination control signal to control light emission of the plurality of light-emitting elements provided in the illumination unit circuit, and an illumination driving unit provided to drive the light-emitting elements according to the illumination control signal input from the illumination control signal output circuit, wherein the light-emitting elements are LEDs, wherein the illumination driving unit is disposed on the imaging element substrate section or the illumination substrate section, and wherein the illumination driving unit includes a transistor array which is formed by a plurality of transistors, the plurality of transistors corresponding to each of the light-emitting elements provided in the illumination unit and generating illumination currents in accordance with the illumination control signal.

2. The capsule endoscope according to claim 1, wherein the illumination control signal output circuit includes:

a voltage-current conversion circuit which is provided to convert a reference voltage into a current, and a control transistor which is provided to form the voltage-current conversion circuit and output a voltage signal generated in accordance with a value of the converted current as the illumination control signal, and wherein the illumination driving unit is configured such that each of the transistors in the transistor array is configured as a driving transistor which is provided to drive the corresponding light-emitting element, and each of the driving transistors generates the illumination current in accordance with a voltage value of the illumination control signal input into gate terminals.

3. The capsule endoscope according to claim 1, wherein the illumination control signal output circuit includes:

a voltage-current conversion circuit which is provided to convert a reference voltage into a current, and a first current mirror circuit which is provided to output a signal of the current in which a value of the current converted by the voltage-current conversion circuit is reproduced as the illumination control signal; and wherein the illumination driving unit includes a plurality of second current mirror circuits corresponding to each of the light-emitting elements, the plurality of second current mirror circuits generating the illumination current obtained by reproducing the value of the current of the illumination control signal by each of the transistors in the transistor array, and the illumination control signal being output from the first current mirror circuit.

4. The capsule endoscope according to claim 1, wherein the illumination control signal output circuit includes an amplifier circuit configured to output a signal of a voltage according to a reference voltage as the illumination control signal, wherein the illumination driving unit further includes a resistor array provided with a plurality of resistors corresponding to the transistors in the transistor array and connected to a reference potential of the amplifier circuit, and wherein each of the transistors in the transistor array is configured as a driving transistor provided to drive the corresponding light-emitting element, and each of the driving transistors is provided to generate the illumination current in accordance with a potential difference between a potential of the illumination control signal input into a gate terminal and a reference potential connected via the corresponding resistor in the resistor array.

5. The capsule endoscope according to claim 2, wherein the illumination control signal output circuit includes an operational amplifier configured to perform comparison of a voltage value of the reference voltage and a voltage value representing the illumination control signal.

6. The capsule endoscope according to claim 1, wherein the illumination driving unit is disposed on the imaging element substrate section, and wherein the illumination driving unit is formed as a component provided in the imaging element mounted on the imaging element substrate section.

* * * * *